US009545244B2

(12) United States Patent
Parihar et al.

(10) Patent No.: US 9,545,244 B2
(45) Date of Patent: Jan. 17, 2017

(54) MECHANICAL TISSUE SAMPLE HOLDER INDEXING DEVICE

(71) Applicant: Devicor Medical Products, Inc., Cincinnati, OH (US)

(72) Inventors: Shailendra Kumar Parihar, Mason, OH (US); Michael Robert Ludzack, Maineville, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 260 days.

(21) Appl. No.: 14/092,139

(22) Filed: Nov. 27, 2013

(65) Prior Publication Data
US 2014/0081170 A1    Mar. 20, 2014

Related U.S. Application Data

(63) Continuation of application No. 12/337,874, filed on Dec. 18, 2008, now Pat. No. 8,622,927.

(51) Int. Cl.
*A61B 10/02* (2006.01)
*A61B 90/00* (2016.01)

(52) U.S. Cl.
CPC .... *A61B 10/0275* (2013.01); *A61B 2010/0208* (2013.01); *A61B 2010/0225* (2013.01); *A61B 2090/0813* (2016.02)

(58) Field of Classification Search
CPC ................ A61B 10/0275; A61B 2010/0208; A61B 2010/0225; A61B 2019/4868
See application file for complete search history.

(56) References Cited

U.S. PATENT DOCUMENTS

| 4,957,492 A | 9/1990 | McVay |
| 5,526,822 A | 6/1996 | Burbank et al. |

(Continued)

FOREIGN PATENT DOCUMENTS

| CN | 101027008 A | 8/2007 |
| CN | 101237822 A | 8/2008 |

(Continued)

OTHER PUBLICATIONS

International Preliminary Patentability Report dated Jun. 21, 2011 for Application No. PCT/US2009/067153.

(Continued)

*Primary Examiner* — Sean Dougherty
(74) *Attorney, Agent, or Firm* — Frost Brown Todd LLC

(57) ABSTRACT

A biopsy device comprises a probe assembly, a holster assembly, a tissue sample holder, and a manually operated rotation mechanism configured to rotate the tissue sample holder. The probe assembly comprises a cutter configured to sever a tissue sample. The tissue sample holder includes a plurality of tissue chambers configured to receive discrete severed tissue samples. The holster assembly comprises the non-motorized, manually operated rotation mechanism configured to allow a user to align consecutive chambers to successively collect discrete severed tissue samples. The tissue sample holder rotation mechanism may comprise a first button, a first lever, a first pawl, a first ratchet, an indexing shaft, and a first gear, which are all configured to, ultimately, rotate a tissue sample holder. The tissue sample holder rotation mechanism may alternately include thumbwheels, a worm gear, or a ratcheting lever, among other things.

19 Claims, 24 Drawing Sheets

(56) References Cited

U.S. PATENT DOCUMENTS

| | | | |
|---|---|---|---|
| 5,904,667 A * | 5/1999 | Falwell | A61M 25/0147 600/146 |
| 6,086,544 A | 7/2000 | Hibner et al. | |
| 6,626,849 B2 | 9/2003 | Huitema et al. | |
| 7,442,171 B2 | 10/2008 | Stephens et al. | |
| 7,575,556 B2 | 8/2009 | Speeg et al. | |
| 7,740,596 B2 | 6/2010 | Hibner | |
| 7,846,107 B2 | 12/2010 | Hoffman et al. | |
| 7,846,109 B2 | 12/2010 | Parihar et al. | |
| 7,938,786 B2 | 5/2011 | Ritchie et al. | |
| 7,981,049 B2 | 7/2011 | Ritchie et al. | |
| 8,052,616 B2 | 11/2011 | Andrisek et al. | |
| 8,118,755 B2 | 2/2012 | Hibner et al. | |
| 8,328,732 B2 | 12/2012 | Parihar et al. | |
| 8,460,206 B2 | 6/2013 | Parihar et al. | |
| 8,622,927 B2 | 1/2014 | Parihar et al. | |
| 2006/0074344 A1 | 4/2006 | Hibner | |
| 2006/0074345 A1 | 4/2006 | Hibner | |
| 2008/0004545 A1 | 1/2008 | Garrison | |
| 2008/0195066 A1 | 8/2008 | Speeg et al. | |
| 2008/0200836 A1 * | 8/2008 | Speeg | A61B 10/0275 600/567 |
| 2008/0214955 A1 | 9/2008 | Speeg et al. | |
| 2009/0131818 A1 | 5/2009 | Speeg et al. | |
| 2009/0131819 A1 | 5/2009 | Ritchie et al. | |
| 2009/0131820 A1 * | 5/2009 | Speeg | A61B 10/0275 600/566 |
| 2009/0131822 A1 * | 5/2009 | Hibner | A61B 10/0275 600/567 |
| 2009/0131823 A1 * | 5/2009 | Andreyko | A61B 10/0096 600/567 |
| 2009/0171243 A1 * | 7/2009 | Hibner | A61B 10/0275 600/566 |
| 2010/0160819 A1 | 6/2010 | Parihar et al. | |
| 2010/0160824 A1 | 6/2010 | Parihar et al. | |

FOREIGN PATENT DOCUMENTS

| | | |
|---|---|---|
| CN | 101297764 A | 11/2008 |
| CN | 101301213 A | 11/2008 |
| CN | 102281820 A | 12/2011 |
| CN | 104013442 A | 9/2014 |
| EP | 1 932482 | 6/2008 |

OTHER PUBLICATIONS

International Search Report dated Feb. 12, 2010 for Application No. PCT/US2009/067153.
Provisional U.S. Appl. No. US 60/869,736, filed Dec. 13, 2006.
Provisional U.S. Appl. No. US 60/874,792, filed Dec. 13, 2006.
Chinese Office Action dated Apr. 1, 2013 for Application No. CN 200980154720.0, 14 pgs.
Chinese Office Action dated Dec. 13, 2013 for Application No. CN 200980154720.0, 9 pgs.
Chinese Office Action dated Jul. 24, 2015 for Application No. CN 201410279688.1, 7 pgs.

* cited by examiner

MECHANICAL TISSUE SAMPLE HOLDER INDEXING DEVICE

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. Merely exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pub. No. 2007/0118048, entitled "Remote Thumbwheel for a Surgical Biopsy Device," published May 24, 2007; U.S. Pub. No. 2008/0214955, entitled "Presentation of Biopsy Sample by Biopsy Device," published Sep. 4, 2008; U.S. Provisional Patent Application Ser. No. 60/869,736, entitled "Biopsy System," filed Dec. 13, 2006; and U.S. Provisional Patent Application Ser. No. 60/874,792, entitled "Biopsy Sample Storage," filed Dec. 13, 2006. The disclosure of each of the above-cited U.S. Patents, U.S. Patent Application Publications, and U.S. Provisional Patent Applications is incorporated by reference herein. While several systems and methods have been made and used for obtaining a biopsy sample, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping biopsy device (100, 1000). It will be further appreciated that for convenience and clarity, spatial and directional terms such as "right," "left," "vertical," "horizontal," "clockwise," and "anti clock-wise" are used herein with respect to the drawings. However, surgical instruments are used in many orientations and positions, and these terms are not intended to be limiting or absolute.

Figure 1:
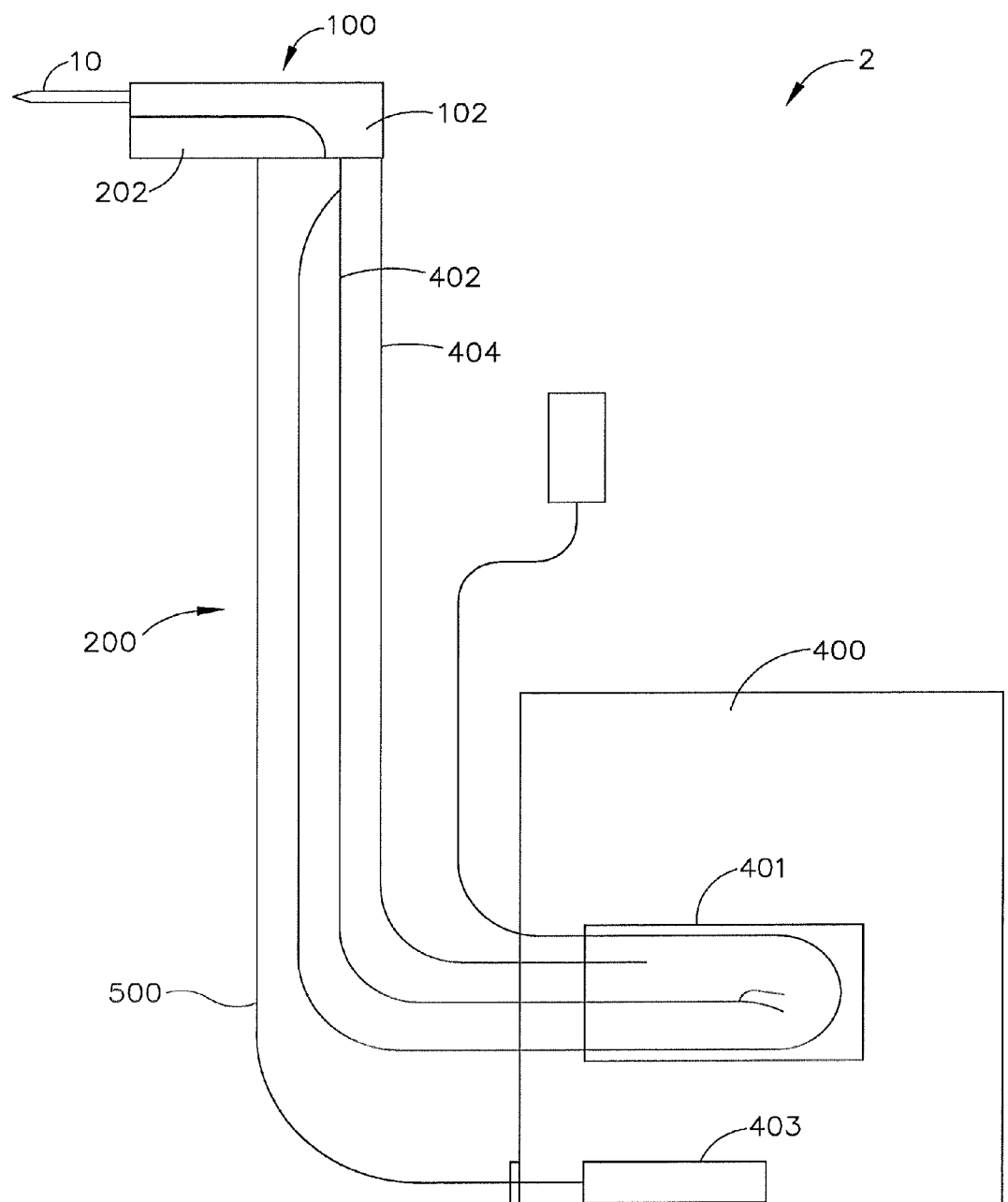
FIG. 1 depicts a schematic view of an exemplary biopsy system.
Figure 2:
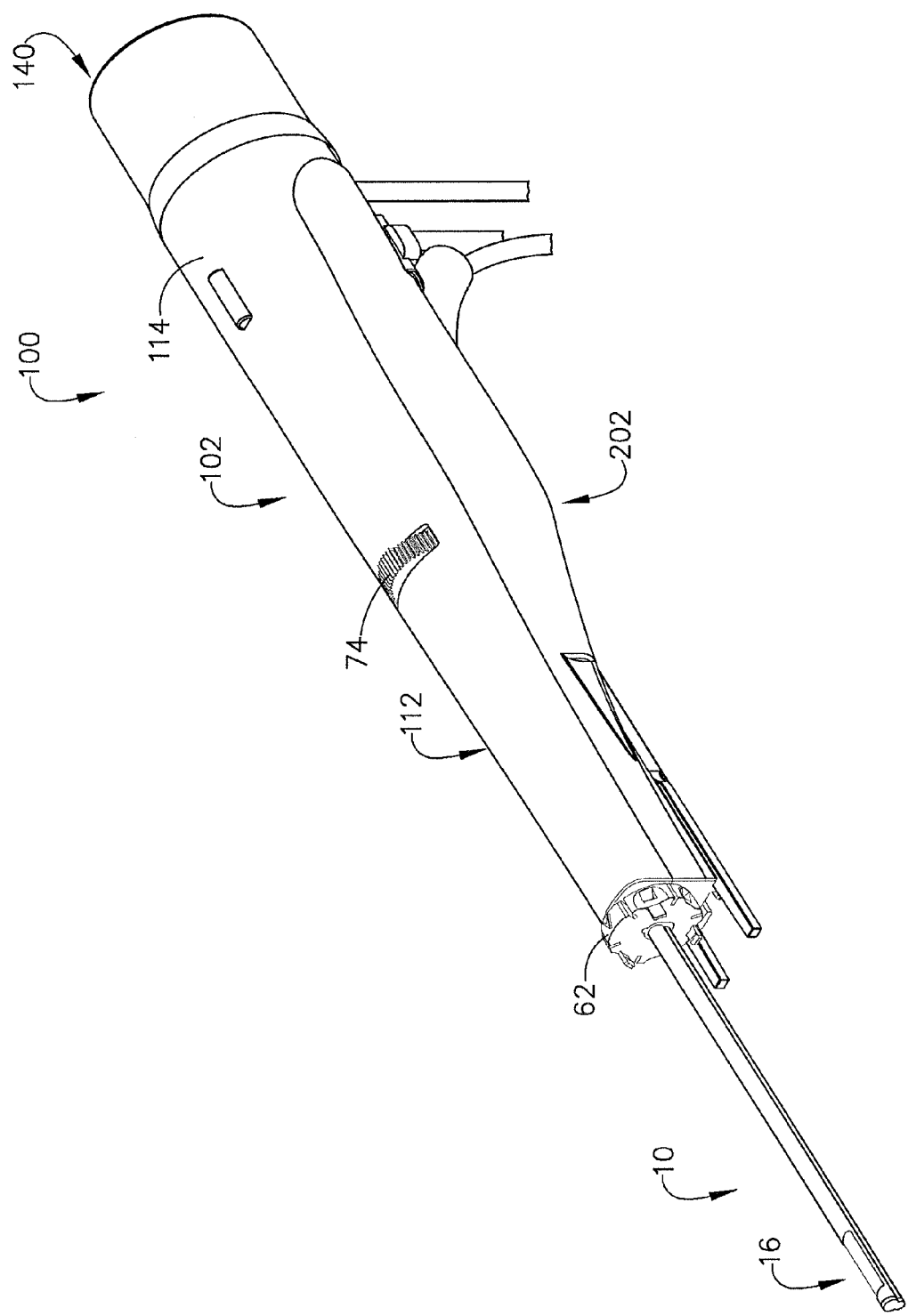
FIG. 2 depicts a perspective view of an exemplary assembled biopsy device.
Figure 3:
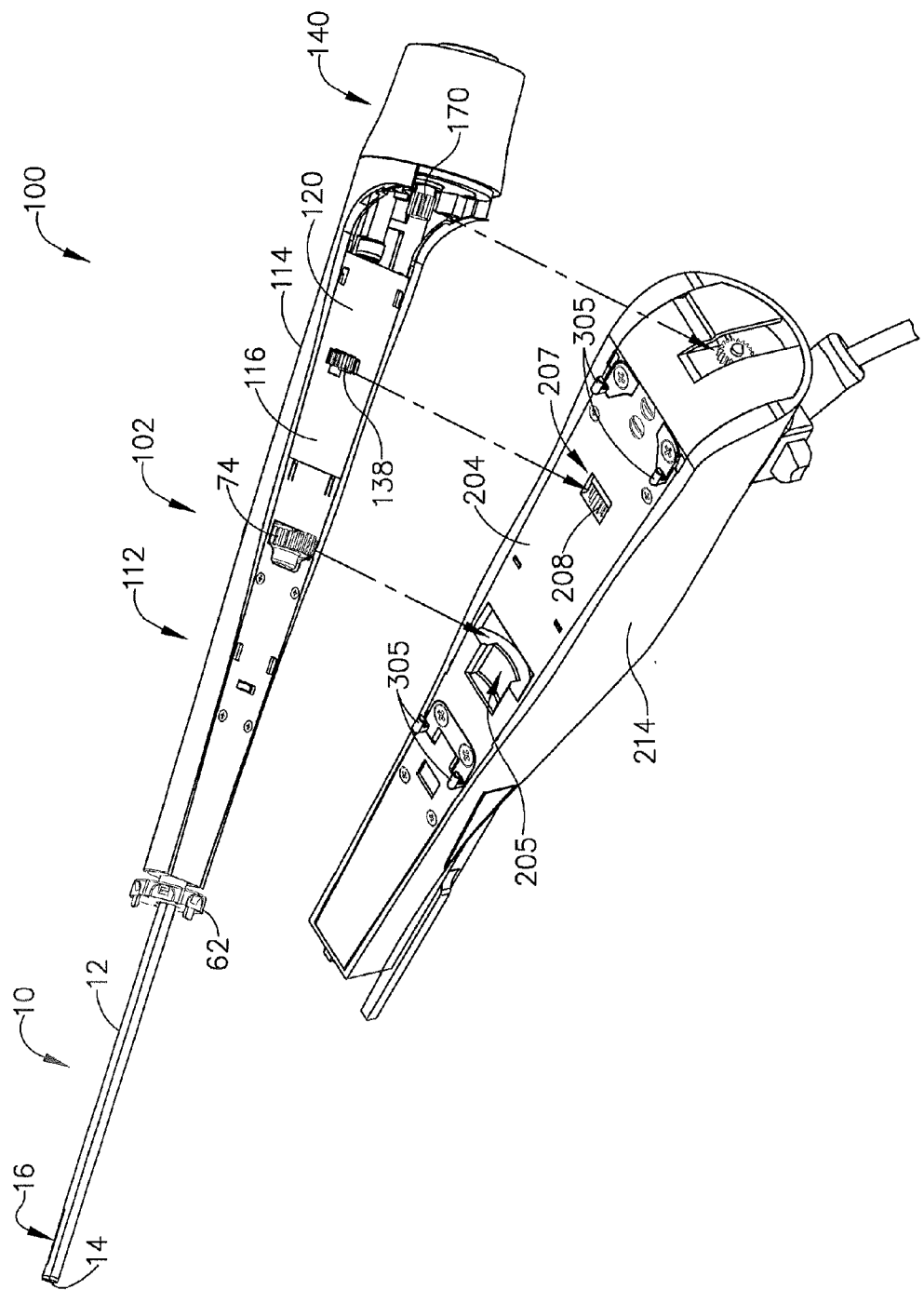
FIG. 3 depicts a perspective view of the biopsy device of FIG. 2, with the probe detached from the holster.
Figure 21:
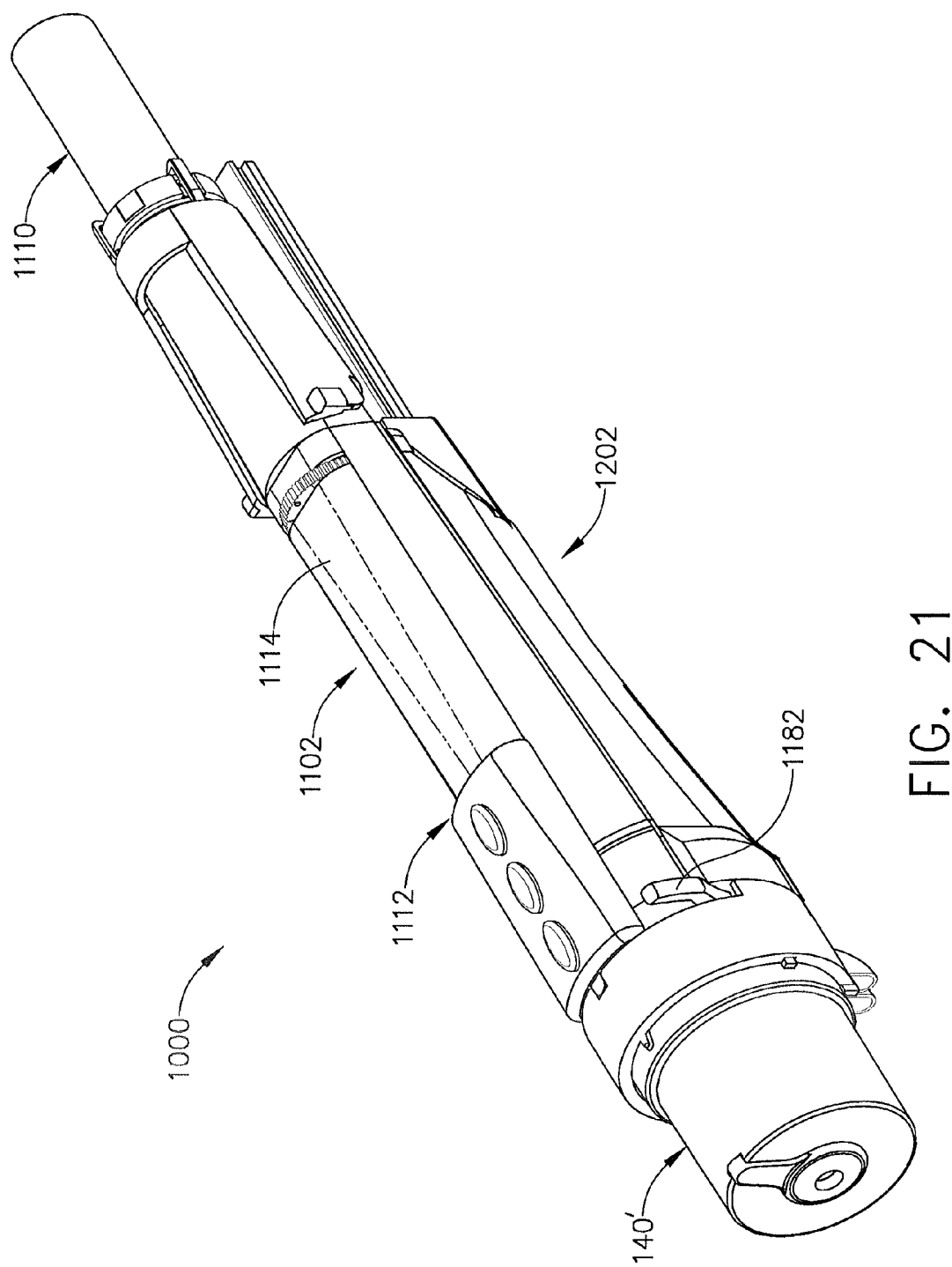
FIG. 21 depicts a perspective view of an exemplary alternative biopsy device.
Figure 22:
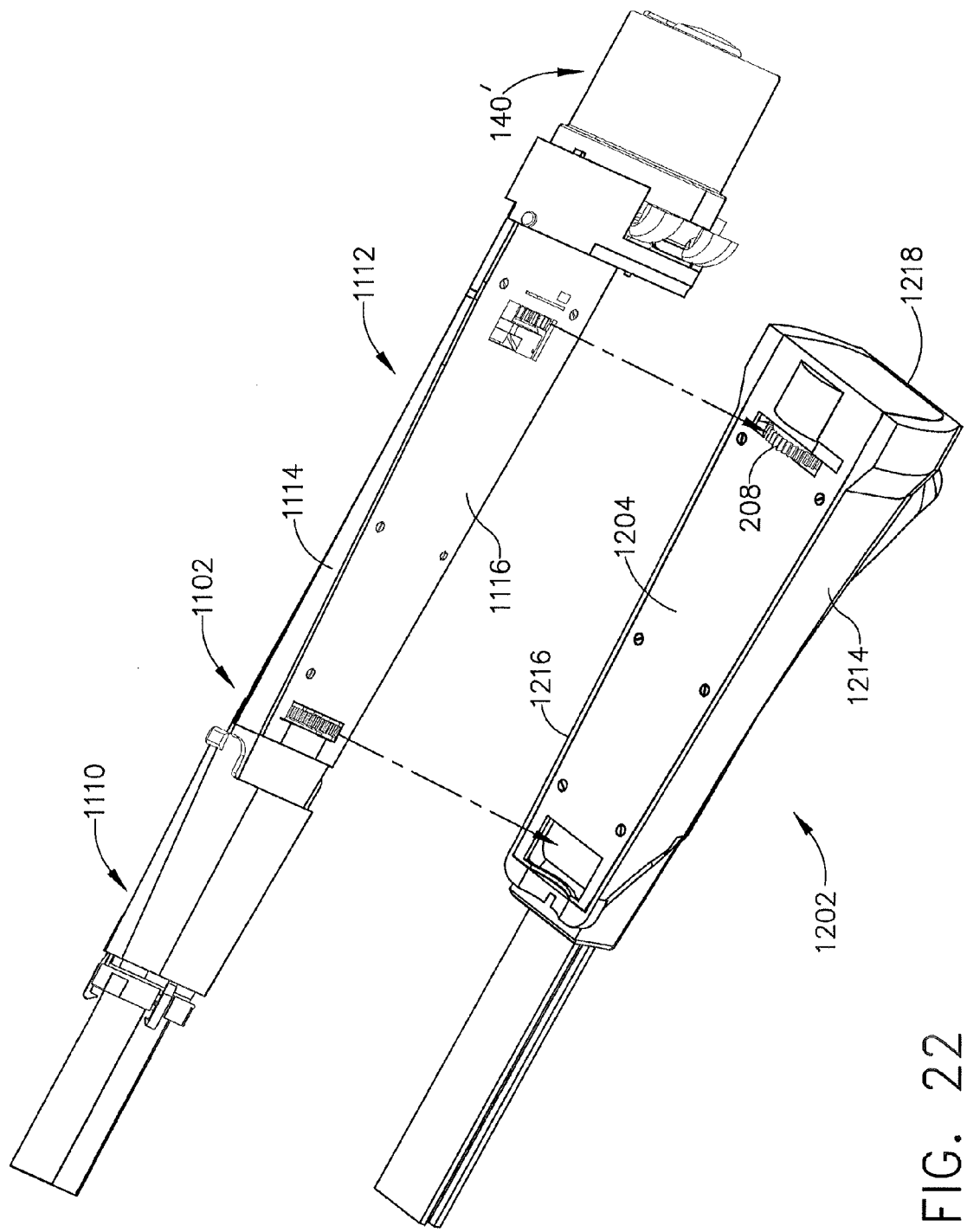
FIG. 22 depicts a perspective view of the biopsy device of FIG. 21, with the probe detached from the holster.
Figure 23:
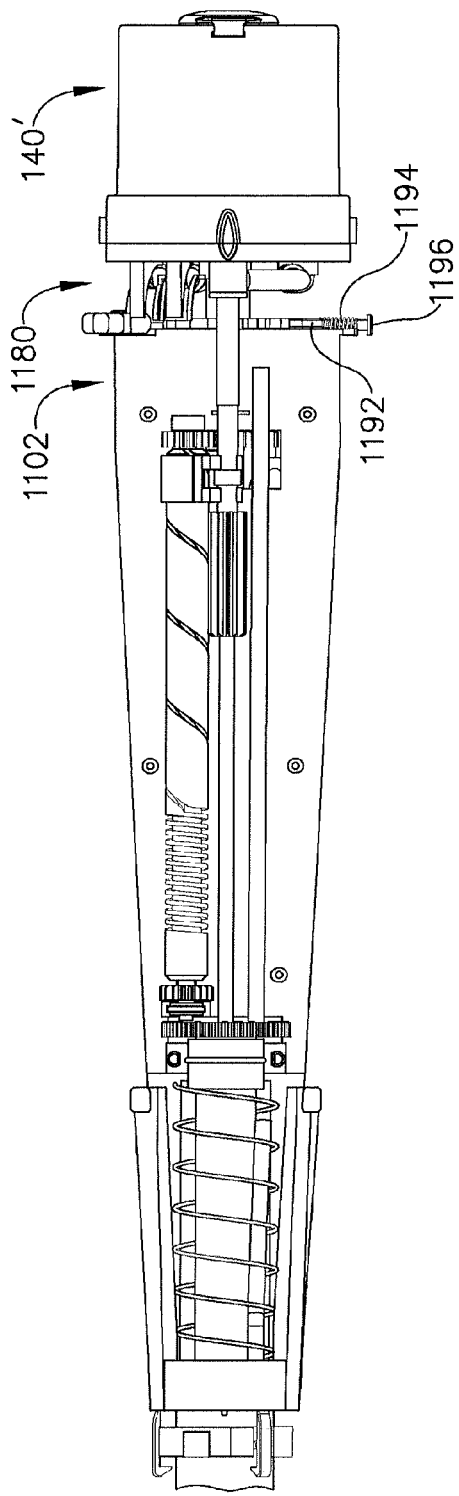
FIG. 23 depicts a top plan view of the probe of the biopsy device of FIG. 21, with a housing component omitted.
Figure 24:
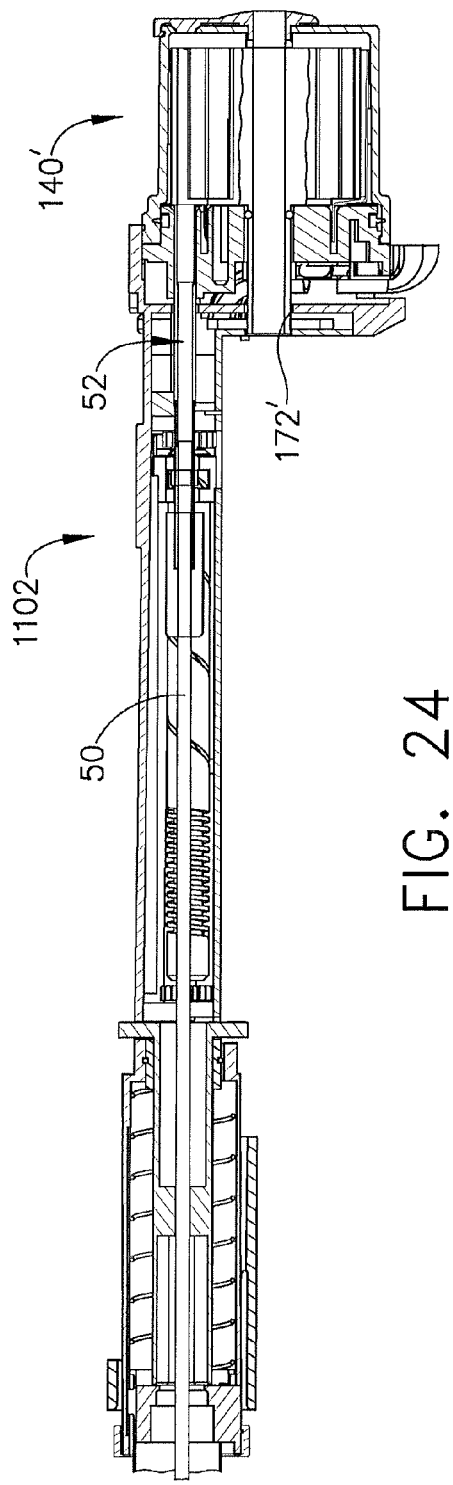
FIG. 24 depicts a side cross-sectional view of the probe of FIG. 23.

As shown in FIG. 1, an exemplary biopsy system (2) includes a biopsy device (100) and a vacuum control module (400). As shown in FIGS. 2-4B, biopsy device (100) comprises a probe (102) and a holster (202). Similarly, as shown in FIGS. 21-22, biopsy device (1000) comprises a probe (1102) and a holster (1202). In addition, alternate embodiments of holsters (702, 802) are shown in FIGS. 14-20.

Those skilled in the art will appreciate that a particular probe embodiment, such as probe (102), may be configured to be coupled with one or more types of holsters, such as holsters (202, 702, 802). Alternatively, a particular holster embodiment, such as holster (202), may be configured to be coupled with one or more probe embodiments, such as probes (102, 1102). As will be described in greater detail below, probes (102, 1102) are separable from their corresponding holsters (202, 702, 802, 1202). Use of the term "holster" herein should not be read as requiring any portion of probe (102, 1102) to be inserted into any portion of holster (202, 702, 802, 1202). Indeed, in some variations of biopsy devices (100, 1000), probe (102, 1102) may simply sit on holster (202, 702, 802, 1202). In some other variations, a portion of holster (202, 702, 802, 1202) may be inserted into probe (102, 1102). Furthermore, in some biopsy devices (100, 1000), probe (102, 1102) and holster (202, 702, 802, 1202) may be of unitary or integral construction, such that the two components cannot be separated. Still other suitable structural and functional relationships between probe (102, 1102) and holster (202, 702, 802, 1202) will be apparent to those of ordinary skill in the art in view of the teachings herein.

Some variations of biopsy devices (100, 1000) may include one or more sensors (not shown), in probe (102, 1102) and/or in holster (202, 702, 802, 1202), that is/are configured to detect when probe (102, 1102) is coupled with holster (202, 702, 802, 1202). Such sensors or other features may further be configured to permit only certain types of probes (102, 1102) and holsters (202, 702, 802, 1202) to be coupled together. In addition or in the alternative, such sensors may be configured to disable one or more functions of probes (102, 1102) and/or holsters (202, 702, 802, 1202) until a suitable probe (102, 1102) and holster (202, 702, 802, 1202) are coupled together. Of course, such sensors and features may be varied or omitted as desired.

One or both of probe (102, 1102) and/or holster (202, 702, 802, 1202) may be provided as a disposable component. Alternatively, one or both of probe (102, 1102) and/or holster (202, 702, 802, 1202) may be provided as a reusable component. Of course, this is not required. By way of example only, probe (102, 1102) may be provided as a disposable component, while holster (202, 702, 802, 1202) may be provided as a reusable component.

Vacuum control module (400) is provided on a cart (not shown) in the present example, though like other components described herein, a cart is merely optional. Among other components described herein, a footswitch (not shown) and/or other devices may be used to provide at least some degree of control of at least a portion of biopsy system (2). Conduits (200) may provide communication of power (e.g., electrical, pneumatic, etc.), control signals, mechanical communication (e.g., via a rotating cable, etc.), saline, vacuum, and venting from vacuum control module (400) to biopsy device (100, 1000). As shown in FIG. 1, a pair of tubes (402, 404) are also coupled with probe (102). One example of a vacuum control module (400) and how it may be used is disclosed in U.S. Pub. No. 2008/0195066, entitled "Revolving Tissue Sample Holder For Biopsy Device," published Aug. 14, 2008, the disclosure of which is incorporated by reference herein.

I. Exemplary Probe

FIGS. 2-4B depict an exemplary embodiment of a probe (102) that is configured to be coupled with each of the holsters (202, 702, 802) shown in FIGS. 2-4B, 7-9, and 14-19. In the illustrated version, probe (102) comprises a needle portion (10) and a body portion (112). Body portion (112) comprises a cover member (114) and a base member (116). A tissue sample holder (140) is removably secured to base member (116), though tissue sample holder (140) may alternatively be secured to cover member (114) or some other component.

A. Exemplary Needle Portion

In the present example, needle portion (10) comprises an outer cannula (12) having a blunt tip (14) and a transverse tissue receiving aperture (16) located proximally from the blunt tip (14). For instance, cannula (12) may be introduced into a patient's breast through a separate cannula (not shown) that has a tissue piercing tip and a aperture configured to align with tissue receiving aperture (16) of outer cannula (12). In alternate embodiments, blunt tip (14) may be replaced with a tissue piercing tip (not shown). Tissue piercing tip may be configured to penetrate tissue without requiring a high amount of force, and without requiring an opening to be preformed in the tissue prior to insertion of the needle portion (10). One suitable configuration for a tissue piercing tip is disclosed in U.S. Pub. No. 2008/0195066, entitled "Revolving Tissue Sample Holder For Biopsy Device," published Aug. 14, 2008, the disclosure of which is incorporated by reference herein. Of course, other suitable configurations for a blunt tip (14) or tissue piercing tip will be apparent to those of ordinary skill in the art in view of the teachings herein.

The interior of outer cannula (12) of the present example defines a cannula lumen (20) and a vacuum lumen (40). By way of example only, outer cannula (12) (and/or any other components of biopsy device (100)) may be configured in accordance with any of the teachings of U.S. Pub. No. 2008/0195066, entitled "Revolving Tissue Sample Holder For Biopsy Device," published Aug. 14, 2008, the disclosure of which is incorporated by reference herein. Alternatively, outer cannula (12) (and/or any other components of biopsy device (100)) may be configured in accordance with any of the teachings of U.S. Non-Provisional patent application Ser. No. 12/337,942, entitled "TISSUE BIOPSY DEVICE WITH CENTRAL THUMBWHEEL," filed on even date herewith, the disclosure of which is incorporated by reference herein. Other ways in which outer cannula (12) may be configured will be apparent to those of ordinary skill in the art in view of the teachings herein.

As shown in FIGS. 2-4B, a needle rotation mechanism (220) comprises a distal thumbwheel (62) and a center thumbwheel (74). Needle rotation mechanism (220) is configured to allow a user to rotate needle portion (10) about its longitudinal axis. In the illustrated version, distal thumbwheel (62) and center thumbwheel (74) are operable to manually rotate outer cannula (12) about its longitudinal axis, relative to cover member (114) and base member (116). For instance, center thumbwheel (74) may be used to orient aperture (16) to a number of desired orientations about the longitudinal axis defined by outer cannula (12). It should be understood that rotation of outer cannula (12) may alternatively be motorized or otherwise provided.

Such multiple orientations may be desirable, by way of example only, to obtain a plurality of tissue samples from a biopsy site, without requiring the needle portion (10) to be removed from the patient during the acquisition of such a plurality of tissue samples. An illustrative example of such rotation and acquisition of multiple tissue samples is disclosed in U.S. Pat. No. 5,526,822, the disclosure of which is incorporated by reference herein. Other ways in which multiple tissue samples may be obtained at various locations will be apparent to those of ordinary skill in the art in view of the teachings herein. For instance, rotation of outer cannula (12) may be motorized or automated using any suitable components or techniques. As another non-exhaustive example, an entire biopsy device (101) may be rotated during acquisition of tissue samples, without necessarily removing biopsy device (100) from the patient during such rotation and tissue sample acquisition, to obtain tissue samples from various orientations about the longitudinal axis defined by outer cannula (12). As yet another merely illustrative example, outer cannula (12) may be rotated by manually rotating a component (e.g., housing component) of tissue sample holder (140). For instance, tissue sample holder (140) may be coupled with outer cannula (12) via a gear train. Examples of such coupling and operation are disclosed in U.S. Non-Provisional patent application Ser. No. 12/337,942, entitled "TISSUE BIOPSY DEVICE WITH CENTRAL THUMB WHEEL," filed on even date herewith, the disclosure of which is incorporated by reference herein. Accurate indexing positions can be achieved using a spring loaded detent (not shown), using a self-aligning mechanism between a housing component of tissue sample holder (140) and the base of probe (100), or using any other suitable components, features, configurations, or techniques.

It will also be appreciated in view of the teachings herein that the orientation of aperture (16) may be indicated on a graphical user interface. For instance, one or more sensors may be operable to detect the orientation of aperture (16), and communicate indicative data to a processor. The processor may be in communication with a display to provide visual indication of aperture (16) orientation. Other ways in which the orientation of aperture (16) may be indicated to a user will be apparent to those of ordinary skill in the art in view of the teachings herein. Alternatively, orientation of aperture (16) may be not indicated to a user.

B. Exemplary Cutter

In the illustrated version, a hollow cutter (50) is disposed within cannula lumen (20). An exemplary embodiment of a cutter (50), together with several variations of the exemplary embodiment, are disclosed in U.S. Pub. No. 2008/0195066, entitled "Revolving Tissue Sample Holder For Biopsy Device," published Aug. 14, 2008, the disclosure of which is incorporated by reference herein. In the embodiment shown in FIGS. 2-4B, the interior of cutter (50) defines a cutter lumen (52), such that fluid and tissue may be communicated through cutter (50) via cutter lumen (52). As will be described in greater detail below, cutter (50) is configured to rotate within cannula lumen (20) and translate axially within cannula lumen (20). In particular, cutter (50) is configured to sever a biopsy sample from tissue protruding through transverse aperture (16) of outer cannula (12). As will also be described in greater detail below, cutter (50) is further configured to permit severed tissue samples to be communicated proximally through cutter lumen (52) to be captured in tissue sample holder (140). Merely illustrative examples of such severing and proximal communication are described in U.S. Pat. No. 5,526,822, the disclosure of which is incorporated by reference herein, though any other suitable structures or techniques may be used for severing and/or communicating tissue samples within a biopsy system (2).

C. Exemplary Cutter Rotation and Translation Mechanism

Figure 4A:
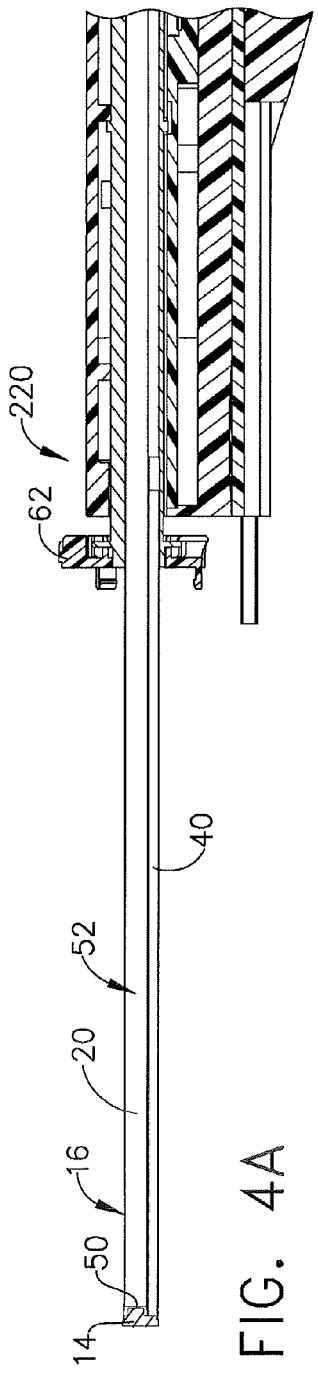
FIG. 4A depicts a partial side cross-sectional view of a distal portion of the biopsy device of FIG. 2, taken along a longitudinal plane.
Figure 4B:
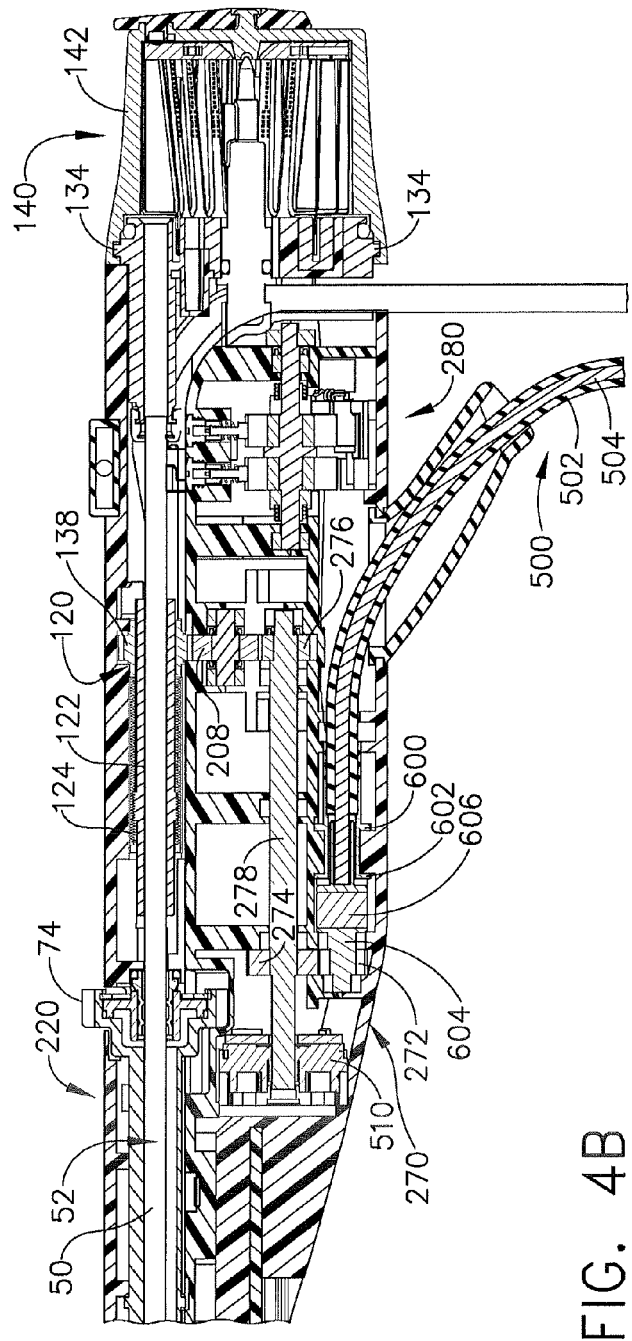
FIG. 4B depicts a partial side cross-sectional view of a proximal portion of the biopsy device of FIG. 2, taken along a longitudinal plane

In the present example, and as shown in FIG. 4B, body portion (112) of probe (102) comprises a cutter rotation and translation mechanism (120), which is operable to rotate and translate cutter (50) within outer cannula (12). Cutter rotation and translation mechanism (120) comprises a sleeve (122) unitarily secured to cutter (50), a nut member (124), and a gear (138). In the present example, gear (138) is partially exposed through base member (116), and is configured to mate with a complementary exposed gear (208) of holster (202), as will be described in greater detail below. In particular, gear (138) is configured to mesh with gear (208) such that gear (208) can impart rotation to gear (138), thereby activating cutter rotation and translation mechanism (120). Gear (208) is in communication with a motor (403) that is external to holster (202, 702, 802). Motor (403) is in communication with gear (208) via a flexible shaft assembly (500). Details of an exemplary cutter rotation and translation mechanism (120) that may be used are disclosed in U.S. Pub. No. 2008/0195066, entitled "Revolving Tissue Sample Holder For Biopsy Device," published Aug. 14, 2008, the disclosure of which is incorporated by reference herein.

It will be appreciated in view of the teachings herein that cutter rotation and translation mechanism (120) described above is merely exemplary, and that translation and/or rotation of cutter (50) may alternatively be provided in various other ways. For instance, biopsy probe (102) may include a motor (not shown) or other device, such that biopsy probe (102) lacks exposed gear (138). Alternatively, any suitable structure other than exposed gear (138) (e.g., a rack, etc.) may be used to receive communication of motion or energy from some other component, in order to rotate and/or translate cutter (50). Furthermore, cutter rotation and translation mechanism (120) may be configured such that more than one exposed gear (138) is present (e.g., one gear (138) for receiving translation motion, and another gear (138) for receiving rotation motion, etc.). In other merely illustrative alternatives, translation and/or rotation of cutter (50) may be performed at least in part by pneumatic actuators (not shown), pneumatic motors (not shown), or a variety of other components. In yet other illustrative alternatives, such as those configured to be used in magnetic resonance imaging environments, translation and/or rotation of cutter (50) may be performed by manually actuated mechanical components without motors or actuators being present in the probe (102) or holster (202). Furthermore, it will be appreciated that pneumatic components may be combined with other mechanical components and/or electro-mechanical components in order to translate and/or rotate cutter (50).

D. Exemplary Tissue Sample Holder and Manifold

As shown in FIGS. 2-4B, a tissue sample holder (140) is provided at the end of body portion (112) of probe (102). In the version shown in FIGS. 5-6, tissue sample holder (140) comprises a cup (142), a manifold (144), and a plurality of trays (160). Manifold (144) includes a central recess (146), a plurality of longitudinal passages (148), a plurality of chambers (150) defined by radially extending walls (152), and plurality of radial passages (154). Descriptions of an exemplary tissue sample holder (140) and tissue sample holder manifold (144) that may be used are disclosed in U.S. Pub. No. 2008/0195066, entitled "Revolving Tissue Sample Holder For Biopsy Device," published Aug. 14, 2008, the disclosure of which is incorporated by reference herein. Of course, any other suitable structures or configurations for tissue sample holder (140) or manifold (144) may be used. By way of example only, one such alternate embodiment of a tissue sample holder is disclosed in U.S. Non-Provisional patent application Ser. No. 12/337,911, entitled "BIOPSY DEVICE WITH DISCRETE TISSUE CHAMBERS," filed on even date herewith, the disclosure of which is incorporated by reference herein. In other words, the tissue sample holders disclosed in that patent application may be configured to be coupled with the probe (102) described herein.

Consequently, tissue sample holder rotation mechanisms (280, 780, 880) described herein may be configured to be used in conjunction with the tissue sample holder disclosed in that patent application as well. Alternatively, any other tissue sample holder may be used.

E. *Exemplary Tissue Sample Trays*

Trays (160) of the illustrated example are configured to be placed on manifold (144), and to receive tissue samples as will be described in greater detail below. Each tray (160) may be rigid, and may be preformed to have a generally arcuate configuration. Alternatively, trays (160) may be formed of a flexible material, such that trays (160) may be bent to conform to the curvature of manifold (144). Alternatively, trays (160) may comprise one or more joints, such that portions of trays (160) may bend or flex at such joints. Still other suitable configurations may be used.

Figure 6:
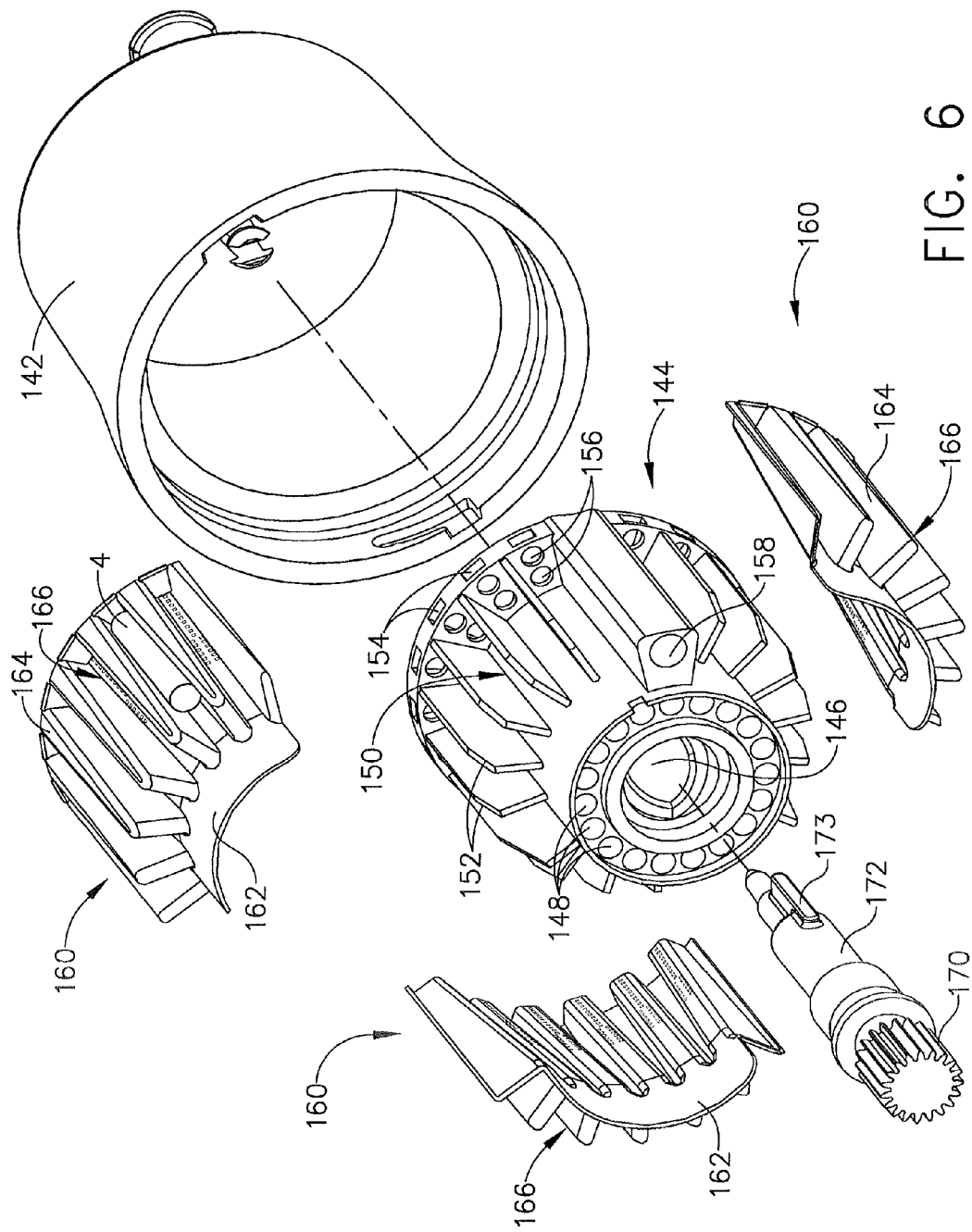
FIG. 6 depicts an exploded perspective view of the tissue sample holder of FIG. 5.
Figure 7:
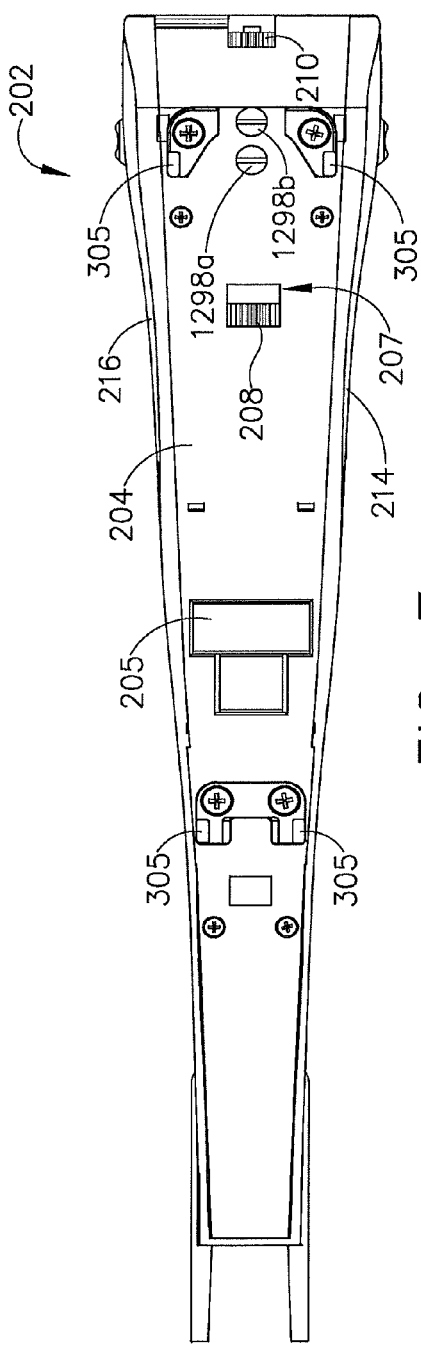
FIG. 7 depicts a top plan view of the holster of the biopsy device of FIG. 2.

Each tray (160) of the present example has a base portion (162) and a plurality of hollow wall portions (164). Hollow wall portions (164) define tissue sample chambers (166). By way of example only, and as shown in FIG. 6, each tissue sample chamber (166) may be configured to receive a single tissue sample (4) captured by cutter (50). Alternatively, tissue sample chambers (166) may be configured such that each tissue sample chamber (166) may hold more than one tissue sample (4). An exemplary tray (160) is disclosed in U.S. Pub. No. 2008/0195066, entitled "Revolving Tissue Sample Holder For Biopsy Device," published Aug. 14, 2008, the disclosure of which is incorporated by reference herein. Other suitable trays that may be used with the devices described herein are disclosed in U.S. Non-Provisional patent application Ser. No. 12/337,911, entitled "BIOPSY DEVICE WITH DISCRETE TISSUE CHAMBERS," filed on even date herewith, the disclosure of which is incorporated by reference herein.

In the present example, manifold (144) and trays (160) provide eighteen chambers (150, 166). Alternatively, any other number of chambers (150, 166) (i.e., more or less than eighteen) may be provided. For instance, in one variation, manifold (144) provides three chambers (150), and three trays (160) are used that each have only one tissue sample chamber (166). In yet another variation, a single tray (160) is used. For instance, a single tray (160) may provide a single large tissue sample chamber (166) or any suitable number of tissue sample chambers (166). Other suitable numbers of chambers (150, 166) and ways in which such chambers (150, 166) may be provided will be apparent to those of ordinary skill in the art in view of the teachings herein. Furthermore, manifold (144) and trays (160) may have any suitable shape. Additional optional modifications for trays (160), such as markings or other indicia, are described in U.S. Pub. No. 2008/0195066, entitled "Revolving Tissue Sample Holder For Biopsy Device," published Aug. 14, 2008, the disclosure of which is incorporated by reference herein.

F. *Exemplary Cup*

Cup (142) is configured to engage bayonets (134) of base member (116), such that cup (142) may be removed from or secured to base member (116) upon sufficient rotation of cup (142) relative to base member (116). Cup (142) may be configured to remain stationary during rotation of manifold (144), as described below. An exemplary embodiment of a cup (142) and additional variations are described in U.S. Pub. No. 2008/0195066, entitled "Revolving Tissue Sample Holder For Biopsy Device," published Aug. 14, 2008, the disclosure of which is incorporated by reference herein.

G. *Exemplary Rotation and Alignment of Manifold*

Manifold (144) of the present example is configured to rotate relative to base member (116), as will be described in greater detail below. As noted above, cup (142) may be configured to remain stationary relative to manifold (144) during rotation and alignment of manifold (144). Manifold (144) of the present example is further configured such that each longitudinal passage (148) may be selectively aligned with a port (not shown) that is in fluid communication with tube (404). Such alignment of a longitudinal passage (148) and the port (not shown) will place the aligned longitudinal passage (148) in fluid communication with tube (404), such that induction of a vacuum within tube (404) will effect induction of a vacuum within longitudinal passage (148), as well as within the chamber (166) associated with that longitudinal passage (148). In addition, manifold (144) and trays (160) of the present example are configured such that each tissue sample chamber (166) may be selectively placed in fluid communication with cutter lumen (52). It will therefore be appreciated that a vacuum in tube (404) may induce a vacuum in cutter lumen (52), with the vacuum being communicated via the port (not shown), an associated longitudinal passage (148), an associated radial passage (154), an associated pair of openings (156), an associated chamber (150), an associated set of openings in tray (160), and an associated tissue sample chamber (166). Of course, there are a variety of other ways in which a vacuum may be induced within a cutter lumen (52), and any other suitable structures or techniques may be used. Furthermore, pressurized air, a liquid (e.g., saline), or any other fluid may be communicated in either direction through the above-mentioned components in lieu of or in addition to a vacuum being induced therein.

A gear (170) is engaged with manifold (144) of the present example. In particular, gear (170) has a shaft (172) that is inserted within central recess (146) of manifold (144). The shaft (172) is configured to engage central recess (146). As shown in FIG. 6, shaft (172) includes a key (173) protruding from shaft (172) which is configured to engage a corresponding keyway (not shown) formed within central recess (146). The engagement between shaft (172) and central recess (146) is such that gear (170), shaft (172), and manifold (144) rotate unitarily. In an alternate illustrative embodiment disclosed in U.S. Pub. No. 2008/0195066, entitled "Revolving Tissue Sample Holder For Biopsy Device," published Aug. 14, 2008, the disclosure of which is incorporated by reference herein, shaft (172) includes flats that are configured to engage corresponding flats formed within central recess (146). Of course, any other suitable structures and methods of engagement between shaft (172) and manifold (144) may be utilized. Alternatively, gear (170) and manifold (144) may have any other suitable configurations or relationships. Nevertheless, gear (170) of the present example may be used to rotate manifold (144), which will in turn permit selective alignment of longitudinal passages (148) with the vacuum port (not shown) of probe (102), in addition to contemporaneously permitting selective alignment of tissue sample chambers (166) with cutter lumen (52). In particular, and as will be described in greater detail below, gear (170) is configured to mesh with a complimentary gear (210, 210', 210") of holster (202, 702, 802), such that gear (210, 210', 210") may be used to impart rotation to gear (170). Such rotation may be used to selectively (e.g., consecutively) align tissue sample chambers (166) with cutter lumen (52), to successively collect a discrete tissue sample (4) in each tissue sample chamber (166) during use of biopsy device (100). Furthermore, such collection of tissue samples (4) may be performed without having to withdraw and re-insert needle portion (10) relative to patient during such a process.

H. Exemplary Dedicated Passage

Figure 5:
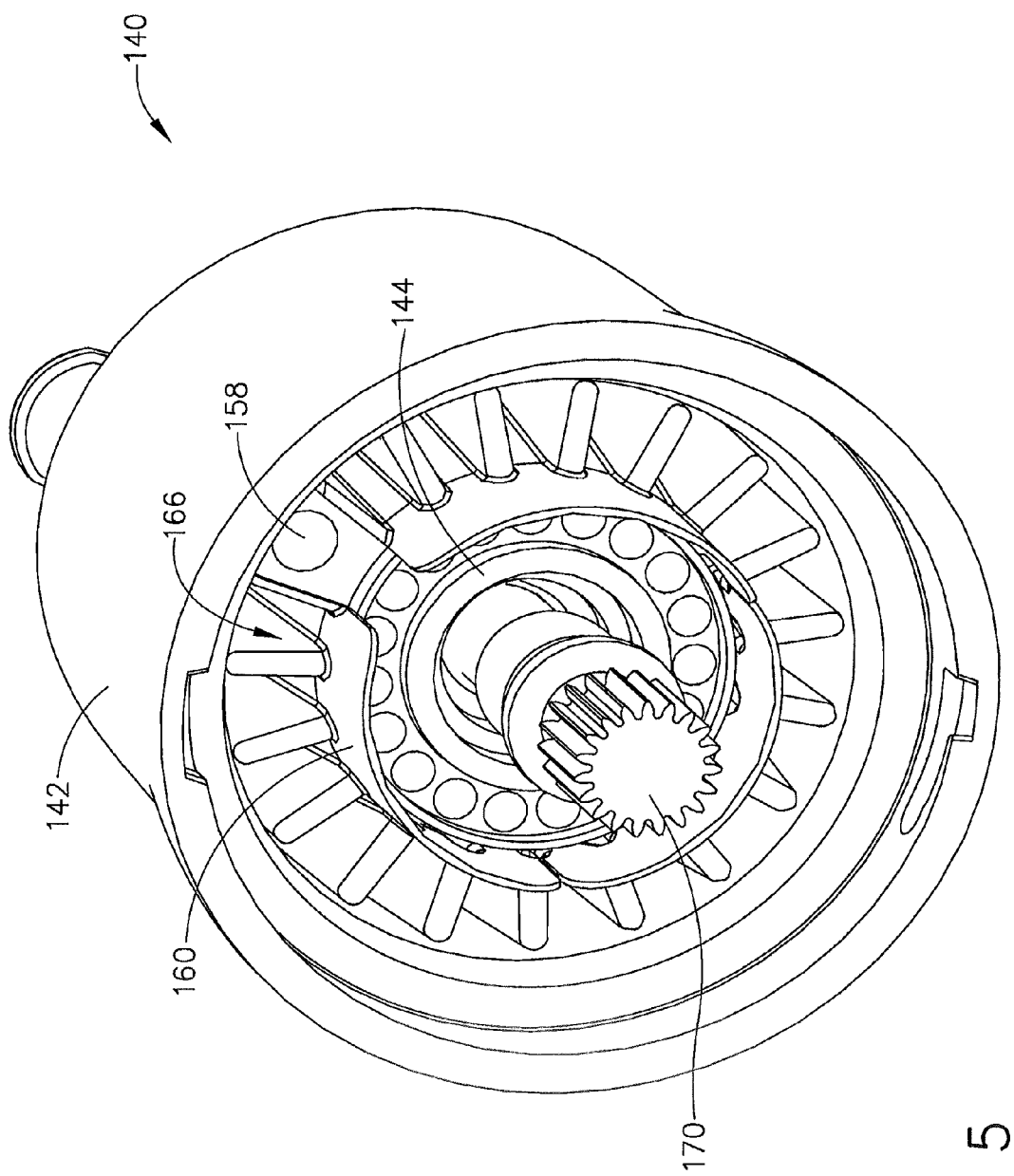
FIG. 5 depicts a front perspective view of an exemplary tissue sample holder.

As shown in FIGS. 5-6, tissue sample holder (140) of the present example has a passage (158) formed through manifold (144). Passage (158) extends longitudinally, completely through manifold (144), and is offset from but parallel with the central axis defined by manifold (144). Like chambers (166), passage (158) of the illustrated version is configured to be selectively aligned with cutter lumen (52). Passage (158) of the present example is configured to permit instruments and/or liquids, other materials, etc., to be passed through manifold (144) and through cutter lumen (52). A detailed description of an exemplary dedicated passage (158) and various uses for passage (158) are disclosed in U.S. Pub. No. 2008/0195066, entitled "Revolving Tissue Sample Holder For Biopsy Device," published Aug. 14, 2008, the disclosure of which is incorporated by reference herein.

As noted above, biopsy probe (102) may be initially provided with a predetermined chamber (166) being aligned with cutter lumen (52) by default. However, in other versions, biopsy probe (102) is initially provided with passage (158) being aligned with cutter lumen (52) by default. Furthermore, to the extent that a user desires having passage (158) aligned with cutter lumen (52) during use of biopsy device (100), after manifold (144) has been rotated during such use, the device may be configured to provide some indication to the user that passage (158) is aligned with cutter lumen (52).

II. Exemplary Holsters

As mentioned above, probe (102) is capable of being coupled with a variety of holsters, including holsters (202, 702, 802) shown in FIGS. 2-4B, 7-9, and 14-19. Each of those exemplary holsters will be described in more detail below. It should be understood, however, that a variety of other holsters may be coupled with probe (102), including but not limited to any holster described in any of the patents, patent application publications, or patent applications cited herein. Furthermore, features of any of the holsters described herein and/or features of any of the holsters described in any of the patents, patent application publications, or patent applications cited herein may be combined in any desired fashion. Accordingly, the holsters (202, 702, 802) described below are mere examples.

A. Push-Button Holster

As shown in FIGS. 2-4B and 7-12, a push-button holster (202) comprises a top cover (204), through which a portion of gear (210) is exposed, sidewalls (214, 216), and a base (218). Holster (202) may be of unitary or integral construction, or, alternatively, top cover (204), sidewalls (214, 216), and base (218) may comprise individual components joined together using fasteners, such as screws, pins, or snap fittings, or any other suitable structures or techniques. Holster (202) of this example further comprises a tissue holder rotation mechanism (280), which will be described in greater detail below.

As noted above, holster (202) of the present example is configured to be coupled with a biopsy probe, such as biopsy probe (102) described above, to provide a biopsy device (100). Of course, holster (202) may also be configured to be coupled with other types of probes. Top cover (204) comprises a recess (205) configured to receive a lower portion of center thumbwheel (74) when probe (102) and holster (202) are engaged. In addition, top cover (204) also comprises opening (207) configured to expose gear (208). As will be described in more detail below, gear (208) is configured to engage gear (138) of cutter rotation and translation mechanism (120). In the illustrated version, a plurality of hook members (305) extend from top housing cover (204) for selectively securing probe (102) to holster (202), though other structures or techniques may be used. In addition, as shown, holster (202) is configured to be handheld, such that biopsy device (100) may be manipulated and operated by a single hand of a user (e.g., using ultrasound guidance, etc.). However, it will be appreciated in view of the disclosure herein that holster (202) may be configured to be mounted to a table, fixture, or other device, such as for use in a stereotactic or X-ray setting, an MRI setting, a PEM setting, a BSGI setting, or any other setting. By way of example only, holster (202) may be coupled with a targeting set, such as the targeting set disclosed in U.S. Non-Provisional patent application Ser. No. 12/337,872, entitled "MULTI-ORIENTATION TARGETING SET FOR MRI BIOPSY DEVICE," filed on even date herewith, the disclosure of which is incorporated by reference herein. Of course, it will be appreciated in view of the disclosure herein that holster (202) may be used in a variety of other settings and combinations.

1. Exemplary Cutter Drive Mechanism

Figure 8:
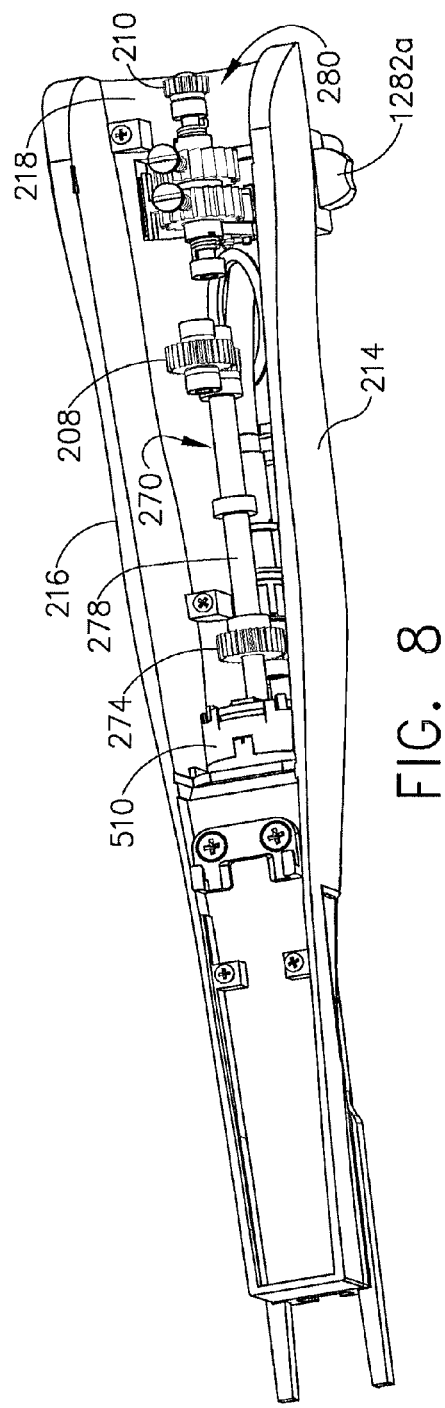
FIG. 8 depicts a top perspective view of the holster of FIG. 7, with a top plate omitted.
Figure 9:
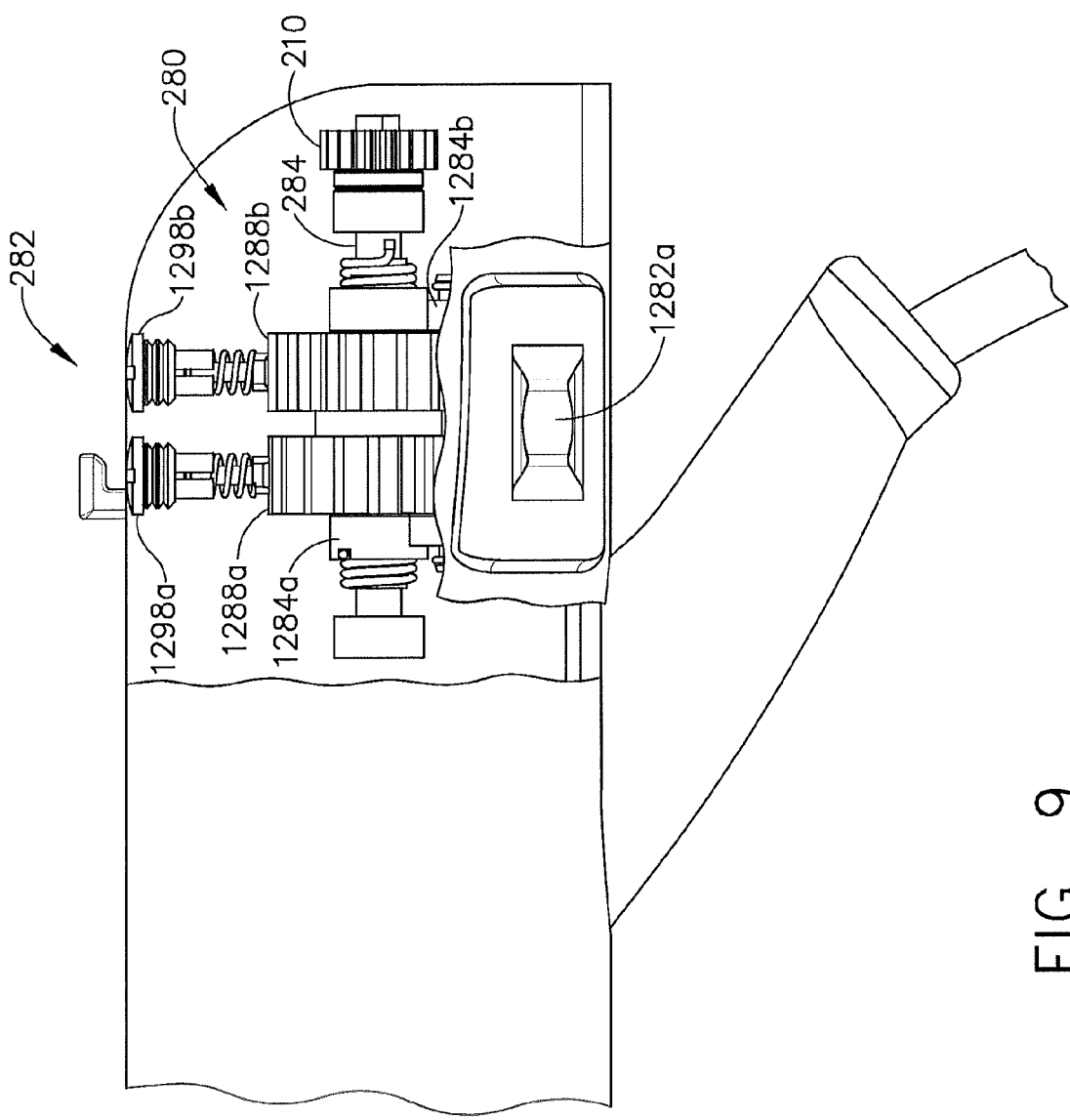
FIG. 9 depicts a partial side view of the holster of FIG. 7, with a portion of the housing removed to reveal the tissue sample holder rotation mechanism.
Figure 10:
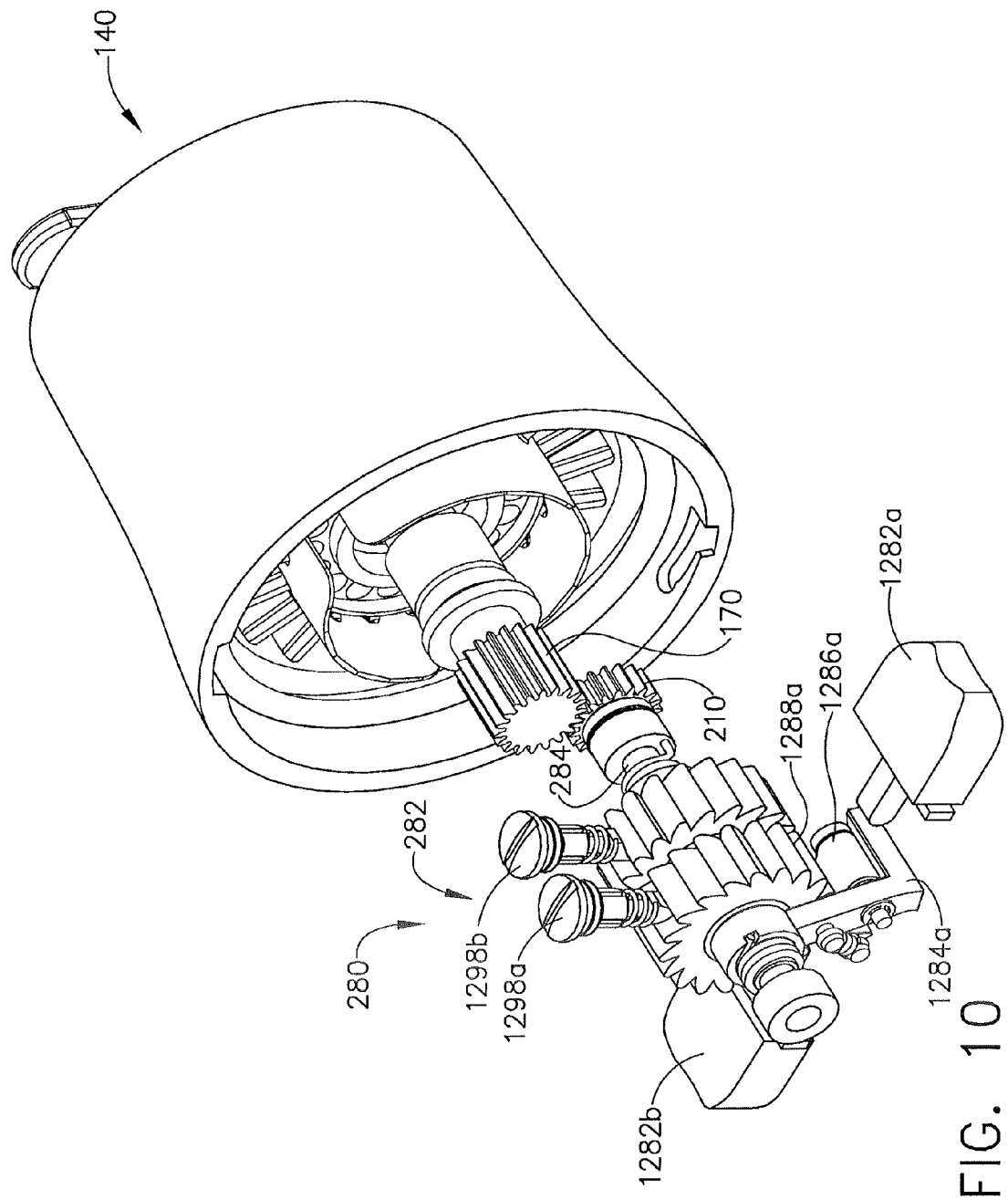
FIG. 10 depicts a top perspective view of the tissue sample holder rotation mechanism of FIG. 9 engaged with the tissue sample holder of FIG. 5.
Figure 11:
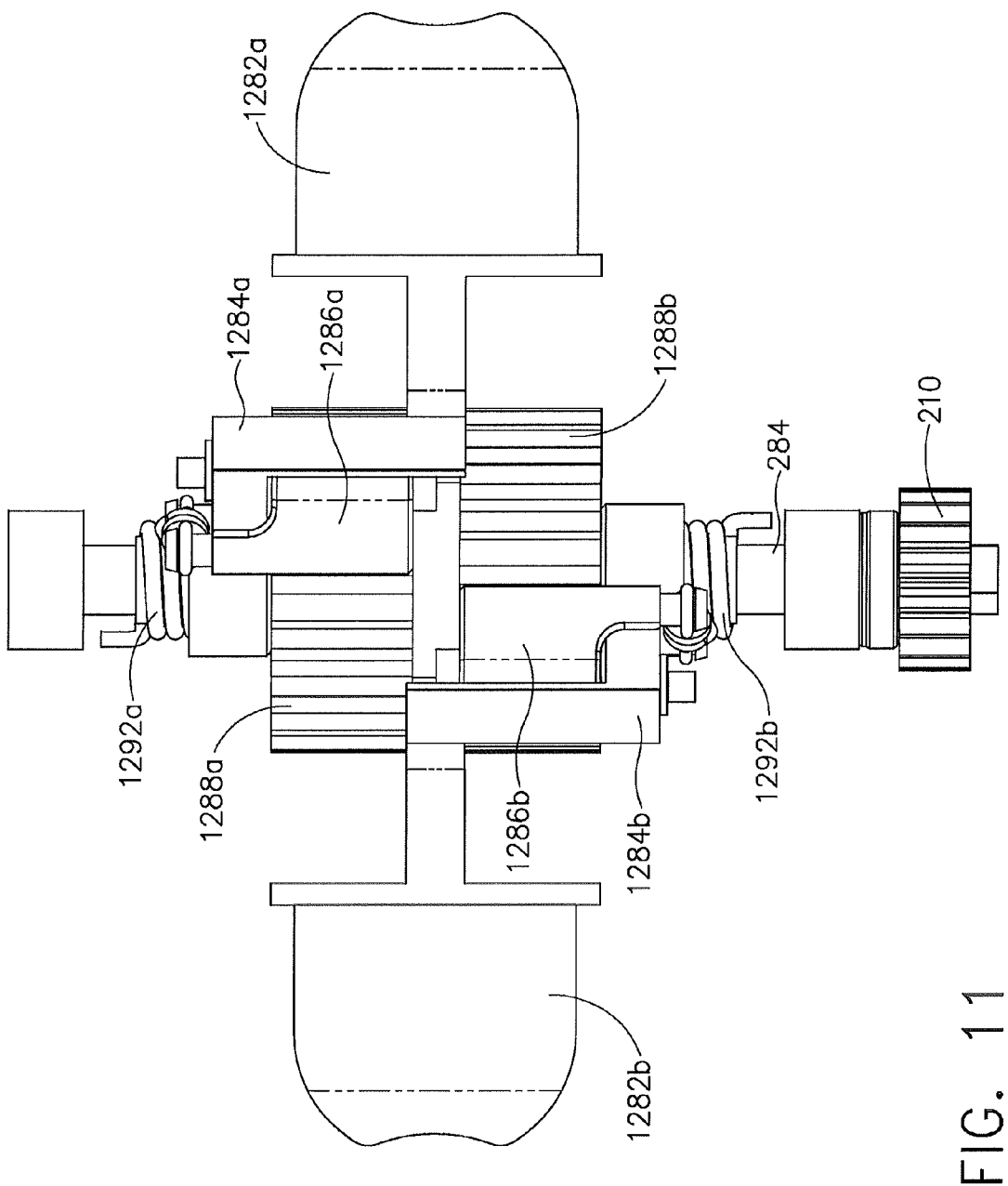
FIG. 11 depicts a bottom plan view of the tissue sample holder rotation mechanism of FIG. 9.
Figure 12:
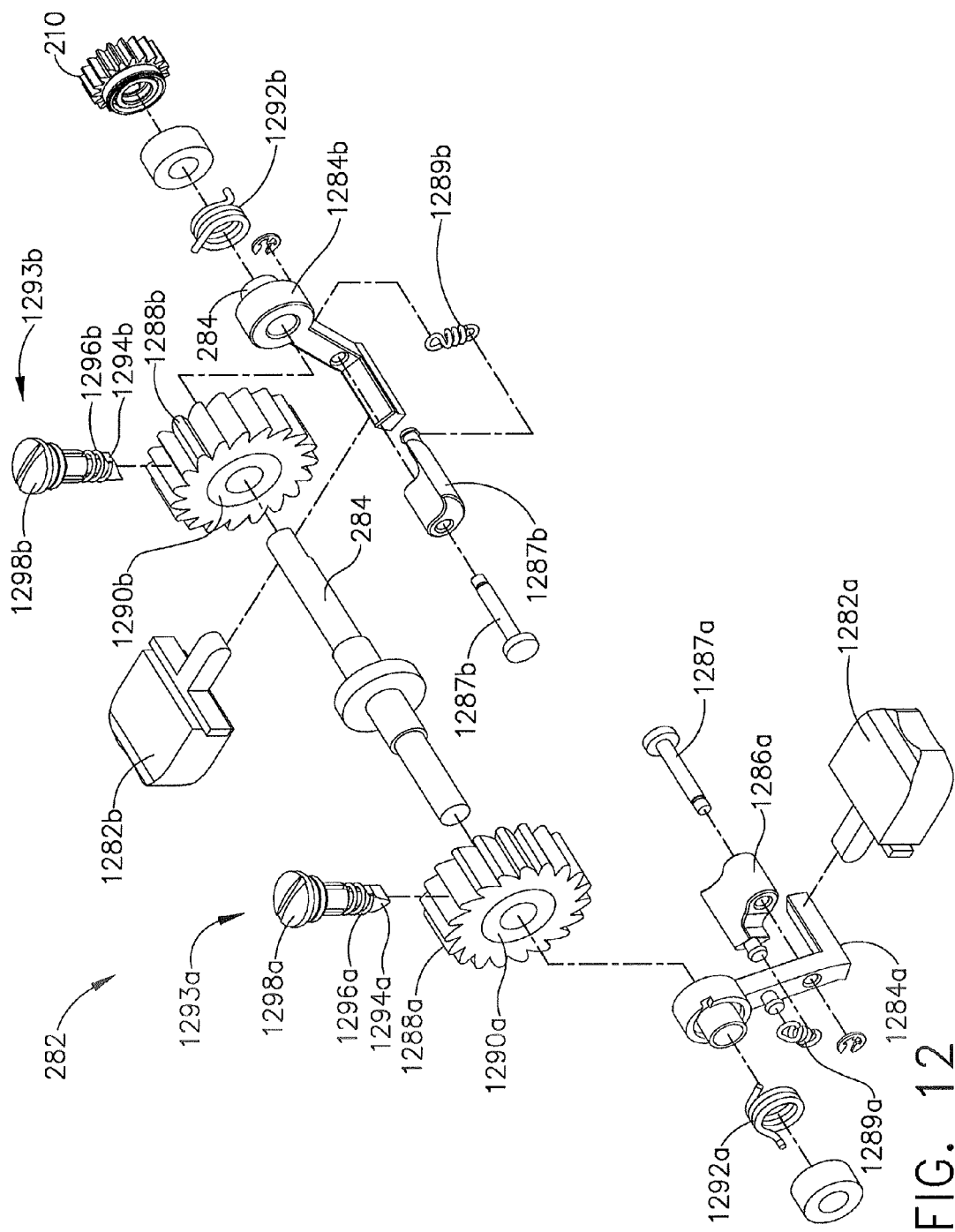
FIG. 12 depicts an exploded perspective view of the tissue sample holder rotation mechanism of FIG. 9.

As shown in FIGS. 4B and 8-9, cutter drive mechanism (270) of the present example comprises a motor (403) that is located externally to or remote from holster (202) and connected to holster (202) via a flexible shaft assembly (500). Flexible shaft assembly (500) comprises an outer casing (502) containing a flexible shaft (504) that is connected to motor (403) at one end and connected to cutter drive mechanism (270) at the other end. To the extent that biopsy device (100) is used in an MRI setting, flexible shaft (504) may be of sufficient length to allow the user to place motor (403) sufficiently far away from any magnetic resonance imaging equipment to avoid interference resulting from any magnetic fields created by the imaging equipment. Flexible shaft (504) may comprise a speedometer type of cable or any other suitable structure or device. Flexible shaft (504) is configured to translate rotational movement of motor (403) to cutter drive mechanism (270). In the illustrated version, cutter drive mechanism comprises gears (208, 272, 274, 276), idler shaft (278), and encoder assembly (510). Flexible shaft (504) is connected to gear (272) via a connector (600), a pair of couplings (602, 604), and a shock absorber (606). Accordingly, when motor (403) is activated to rotate, such rotation may be communicated via flexible shaft (504) to gear (272). Of course, other suitable structures and methods for connecting flexible shaft (504) to gear (272) will be apparent to those of ordinary skill in the art, as will other structures and methods for effecting rotation of gear (272) or other components of cutter drive mechanism (270).

Gear (272) is configured to mesh with gear (274) such that rotation of gear (272) results in corresponding rotation of gear (274). Gear (274) is mounted to idler shaft (278) and is configured to rotate unitarily therewith. Encoder assembly (510) is mounted on the distal end of idler shaft (278). Encoder assembly (510) may be configured to gather information indicative of the rotational and translational position of cutter (50). One suitable configuration for an encoder assembly is disclosed in U.S. Pub. No. 2008/0195066, entitled "Revolving Tissue Sample Holder For Biopsy Device," published Aug. 14, 2008, the disclosure of which is incorporated by reference herein, though any other type of encoder assembly may be used. Suitable substitutes for encoder assembly (510) will be apparent to those of ordinary skill in the art, including but not limited to combinations of magnets and hall effect sensors, light sources and photosensors, etc. Examples of how encoder assembly (510) may be used are disclosed in U.S. Non-Provisional patent application Ser. No. 12/337,942, entitled "TISSUE BIOPSY DEVICE WITH CENTRAL THUMB WHEEL," filed on even date herewith, the disclosure of which is incorporated by reference herein, though encoder assembly (510) may be used in any other suitable way, to the extent that an encoder assembly (510) is included at all.

Gear (276) is mounted adjacent to the proximal end of idler shaft (278) and is configured to rotate unitarily therewith. Gear (276) is configured to mesh with gear (208) such that rotation of gear (276) results in corresponding rotation of gear (208). As noted above, a portion of gear (208) is exposed through top cover (204), such that gear (208) meshes with gear (138) of cutter rotation and translation mechanism (120) when biopsy probe (102) is coupled with holster (202). Accordingly, when motor (not shown) is activated to rotate, such rotation may be communicated via flexible shaft (504), gears (208, 272, 274, 276) and idler shaft (278), to effect simultaneous rotation and translation of cutter (50) as described above. Other ways in which a cutter drive mechanism (270) may be configured or operated will be apparent to those of ordinary skill in the art in view of the teachings herein.

2. Exemplary Tissue Holder Rotation Mechanism

As shown in FIGS. 8-12, holster (202) includes a tissue holder rotation mechanism (280). Tissue holder rotation mechanism (280) may be designed to be compatible for use in a magnetic environment, for instance within a magnetic resonance imaging environment. The use of certain electric motors may be restricted in magnetic environments, such as those where magnetic resonance imaging is accomplished. Tissue holder rotation mechanism (280) of the present example incorporates manually actuated mechanical components to index tissue sample holder (140), instead of electric motors or other actuators, such as electric, piezoelectric or pneumatic actuators. Exemplary tissue holder rotation mechanism (280) also comprises manual controls (i.e. buttons (1282a, 1282b)), rather than digital or electrical controls. The manual controls may provide high reliability, such as in an MRI environment. Of course alternative components, such as electric motors or other actuators and digital or electrical controls, may be used in alternate embodiments.

In the illustrated version, tissue holder rotation mechanism (280) comprises an actuation mechanism (282) having a shaft (284) with a gear (210) mounted thereto, such that during an actuation stroke of actuation mechanism (282), gear (210) rotates unitarily with shaft (284). In the illustrated example, actuation mechanism (282) comprises two sets of components, including a pair of buttons (1282a, 1282b), a pair of levers (1284a, 1284b), a pair of pawls (1286a, 1286b), a pair of ratchets (1288a, 1288b), a pair of one-way clutches (1290a, 1290b), a pair of torsion springs (1292a, 1292b), a pair of reciprocating pawls (1294a, 1294b), a pair of compression springs (1296a, 1296b) and a pair of top caps (1298a, 1298b). In the illustrated example, one set of components (for example 1282a, 1284a, 1286a, 1288a, 1290a, 1292a, 1294a, 1296a, and 1298a) is configured to allow a user to rotate the tissue sample holder manifold (144) in a clockwise direction, while the other set of components (for example 1282b, 1284b, 1286b, 1288b, 1290b, 1292b, 1294b, 1296b, and 1298b) is configured to allow a user to rotate the tissue sample holder manifold (144) in a counterclockwise direction. Of course, this orientation may be reversed so that button (1282a) initiates anti clockwise rotation and button (1282b) initiates clockwise rotation. Alternatively, a holster (not shown) may only include one button and corresponding set of components configured to provide unidirectional rotation of the tissue sample holder, instead of the bidirectional rotation provided for in the illustrated embodiment. During an actuation stroke, a user depresses one of the pair of buttons (1282a, 1282b) which causes the tissue sample holder (140) to rotate and advance by one chamber (150, 166) and selectively align a consecutive chamber (150, 166) with cutter lumen (52). The actuation stroke will be discussed in more detail below.

As shown in FIGS. 2-3 and 7-9, buttons (1282a, 1282b) are positioned along and extend through side panels (214, 216). Buttons (1282a, 1282b) may be positioned such that when probe (102) and holster (202) are engaged, a user is able to depress one of buttons (1282a, 1282b) while grasping biopsy device (100) with one hand. The dual button configuration, as shown in FIGS. 2-3 and 7-13, also may permit a user to use either his/her right or left hand to grasp biopsy device (100) and index tissue sample holder (140) by depressing one of buttons (1282a, 1282b).

As mentioned above, the illustrated version of actuation mechanism (282) comprises two sets of components: set #1—1282a, 1284a, 1286a, 1288a, 1290a, 1292a, 1294a, 1296a, and 1298a; and set #2—1282b, 1284b, 1286b, 1288b, 1290b, 1292b, 1294b, 1296b, and 1298b. The two sets of components are essentially identical in configuration and function, except for the fact that set #1 is configured to produce clockwise rotation of tissue sample holder (140) and set #2 is configured to produce counterclockwise rotation of tissue sample holder (140). Of course, as mentioned above, the orientation of these two sets of components may be reversed so that set #1 produces counterclockwise rotation and set #2 produces clockwise rotation of tissue sample holder (140).

As shown in FIGS. 8-12, button (1282a) is in mechanical communication with lever (1284a). Pawl (1286a) is attached to lever (1284a) and is configured to engage one of the plurality of teeth on ratchet (1288a). Pawl (1286a) is therefore operable to rotate ratchet (1288a) in response to actuation of lever (1284a) by a user pressing button (1282a). Pawl (1286a) is configured to rotate about pin (1287a), while spring (1289a) biases pawl (1286a) against ratchet (1288a). Similarly, in the illustrated version, button (1282b) is in mechanical communication with lever (1284b). Pawl (1286b) is attached to lever (1284b) and is configured to engage one of the plurality of teeth on ratchet (1288a). Pawl (1286b) is therefore operable to rotate ratchet (1288b) in response to actuation of lever (1284b) by a user pressing button (1282b). Pawl (1286b) is configured to rotate about pin (1287b), while spring (1289b) biases pawl (1286b) against ratchet (1288b).

In the present example, ratchets (1288a, 1288b) include nineteen teeth, which corresponds to the number of chambers (150, 166) (including dedicated passage (158)) in the tissue sample holder (140). The correlation between the number of teeth on ratchets (1288a, 1288b) and the number of chambers (150, 166) in the tissue sample holder (140) may ensure that each actuation stroke of actuation mechanism (282) indexes the tissue sample holder (140) one chamber (150) at a time. However, this is not required.

Ratchets (1288a, 1288b) may comprise any suitable number of teeth, and need not necessarily correspond directly or indirectly with the number of chambers (150, 166).

As shown in FIGS. 8-12, actuation mechanism (282) comprises a pair of rotation restriction assemblies (1293a, 1293b), which comprise reciprocating pawls (1294a, 1294b), compression springs (1296a, 1296b), and top caps (1298a, 1298b). In this version, rotation restriction assemblies (1293a, 1293b) are configured to allow ratchets (1288a, 1288b) to rotate in one direction, while preventing ratchets (1288a, 1288b) from rotating in the reverse direction. For example, in the illustrated version, rotation restriction assembly (1293a) is configured to prevent ratchet (1288a) from rotating in a clockwise direction, while rotation restriction assembly (1293b) is configured to prevent ratchet (1288b) from rotating in a counterclockwise direction. Such unidirectional movement may be provided by cooperative shapes or configurations of pawls (1294a, 1294b) and teeth of ratchets (1288a, 1288b).

As shown in FIGS. 7-12, top cap (1298a) is configured to be attached to top cover (204) and to allow pawl (1294a) to travel vertically upward during clockwise rotation of ratchet (1288a). Compression spring (1296a) is positioned between top cap (1298a) on an upper end and pawl (1294a) on a lower end. In this embodiment, pawl (1294a) releasably engages one of the teeth of ratchet (1288a) and includes a cam profile configured to cause pawl (1294a) to travel vertically during counterclockwise rotation of ratchet (1288a) before re-engaging the next tooth of ratchet (1288a). Compression spring (1296a) may be configured to allow pawl (1294a) to travel vertically upward during counterclockwise rotation of ratchet (1288a), while concomitantly urging pawl (1294a) downward toward re-engagement with ratchet (1288a).

Similarly, as shown in FIGS. 7-12, top cap (1298b) is configured to be attached to top cover (204) and to allow pawl (1294b) to travel vertically upward during clockwise rotation of ratchet (1288b). Compression spring (1296b) is positioned between top cap (1298b) on an upper end and pawl (1294b) on a lower end. In this version, pawl (1294b) engages one of the teeth of ratchet (1288b) and includes a cam profile configured to cause pawl (1294a) to travel vertically during clockwise rotation of ratchet (1288a) before re-engaging the next tooth of ratchet (1288b). Compression spring (1296b) may be configured to allow pawl (1294b) to travel vertically upward during clockwise rotation of ratchet (1288b), while concomitantly urging pawl (1294b) downward toward re-engagement with ratchet (1288b). Of course, as mentioned above, the orientation of the rotation of ratchets (1288a, 1288b) may be reversed.

As shown, actuation mechanism (282) further comprises a pair of one-way clutches (1290a, 1290b), which are configured to ensure unidirectional rotation of ratchets (1288a, 1288b) respectively. One-way clutch (1290a) is positioned within a central opening in ratchet (1288a) between ratchet (1288a) and shaft (284). One-way clutch (1290a) is configured to communicate counterclockwise rotation of ratchet (1288a) into counterclockwise rotation of shaft (284). One-way clutch (1290b) is similarly situated between ratchet (1288b) and shaft (284) and configured to communicate clockwise rotation of ratchet (1288b) into clockwise rotation of shaft (284). Of course, as mentioned above, the orientation of the rotation provided by ratchets (1288a, 1288b) and one-way clutches (1290a, 1290b) may be reversed.

Finally, in the illustrated example, actuation mechanism (282) comprises a pair of torsion springs (1292a, 1292b) configured to urge levers (1284a, 1284b) and buttons (1282a, 1282b) toward their original position upon completion of an actuation stroke. In particular, torsion spring (1292a) is positioned along shaft (284) and engages lever (1284a), while torsion spring (1292b) is positioned along shaft (284) and engages lever (1284b). In the illustrated version, torsion spring (1292a) is positioned distally along shaft (284) relative to torsion spring (1292b). The interaction between torsion springs (1292a, 1292b) and levers (1284a, 1284b) will be described in more detail below.

3. Exemplary Actuation Stroke

The tissue holder rotation mechanism (280) depicted in FIGS. 8-12 is configured to index the tissue holder (140) by one chamber (150, 166) during a single actuation stroke, thereby allowing a user to align successive chambers (150, 166) with cutter lumen (52) to receive successive tissue samples (4). This functionality may facilitate collection of multiple tissue samples (4) without requiring the user to remove biopsy device (100) from the patient. Of course, tissue holder rotation mechanism (780) may be configured to index tissue holder (140) any suitable number of chambers (150, 166) during a single actuation stroke.

In the illustrated version, an actuation stroke producing clockwise rotation (viewing from tissue sample holder (140) toward needle portion (10)) of manifold (144) may be induced by depressing button (1282a), which causes lever (1284a) to move inward, thereby causing pawl (1286a) to engage one of the plurality of teeth on ratchet (1288a). The movement of these components causes ratchet (1288a) to rotate in a counterclockwise direction. As ratchet (1288a) rotates, pawl (1294a), which is engaged with a tooth on ratchet (1288a) is forced vertically upward by the tooth, thereby compressing compression spring (1296a). As ratchet (1288a) rotates, the tooth disengages from pawl (1294a), and pawl (1294a) is urged vertically downward by compression spring (1292a) and engages the successive tooth on ratchet (1288a). The re-engagement of ratchet (1288a) by pawl (1294a) prevents reverse rotation of ratchet (1288a). As ratchet (1288a) rotates, the rotation is translated to shaft (284) via one-way clutch (1290a). As mentioned above, shaft (284) and gear (286) rotate unitarily. The resulting rotation of gear (286) will thus cause rotation of gear (170), thereby causing rotation of manifold (144) to align the next chamber (150, 166) with cutter lumen (52). Upon completion of the actuation stroke, lever (1284a) and button (1282a) are urged toward their original, pre-actuation position by torsion spring (1292a). Spring (1289a) and pin (1287a) allow pawl (1286a) to rotate to "ride over" an adjacent tooth of ratchet (1288a) as lever (1284a) returns to its pre-actuation position under urging of torsion spring (1292a); while spring (1289a) urges pawl (1286a) back into the valley between the next teeth of ratchet (1288a) as lever (1284a) reaches its pre-actuation position.

Similarly, in the illustrated version, an actuation stroke to produce counterclockwise rotation (viewing from tissue sample holder (140) toward needle portion (10)) of manifold (144) may be induced by depressing button (1282b), which causes lever (1284b) to move inward, thereby causing pawl (1286b) to engage one of the plurality of teeth on ratchet (1288b). The movement of these components causes ratchet (1288b) to rotate in a clockwise direction. As ratchet (1288b) rotates, pawl (1294b), which is engaged with a tooth on ratchet (1288b) is forced vertically upward by the tooth, thereby compressing compression spring (1296b). As ratchet (1288b) rotates, the tooth disengages from pawl (1294b), and pawl (1294b) is urged vertically downward by compression spring (1292b) and engages the successive tooth on ratchet (1288b). The re-engagement of ratchet (1288b) by pawl (1294b) prevents reverse rotation of ratchet (1288b). As ratchet (1288b) rotates, the rotation is translated to shaft (284) via one-way clutch (1290b). As mentioned above, shaft (284) and gear (286) rotate unitarily. The resulting rotation of gear (286) will thus cause rotation of gear (170), thereby causing rotation of manifold (144) to align the next chamber (150, 166) with cutter lumen (52). Upon completion of the actuation stroke, lever (1284b) and button (1282b) are urged toward their original, pre-actuation position by torsion spring (1292b). Spring (1289b) and pin (1287b) allow pawl (1286b) to rotate to "ride over" an adjacent tooth of ratchet (1288b) as lever (1284b) returns to its pre-actuation position under urging of torsion spring (1292b); while spring (1289b) urges pawl (1286b) back into the valley between the next teeth of ratchet (1288b) as lever (1284b) reaches its pre-actuation position.

The rotation generated by the actuation stroke is communicated from the actuation mechanism (282) to manifold (144) via shaft (284) and gear (210), which are configured to rotate unitarily. As noted above, gear (210) is configured to be at least partially exposed through the proximal surface of top cover (204) and to mesh with gear (170) of tissue sample holder (140) when biopsy probe (102) is coupled with holster (202). Rotation of shaft (284) and gear (210) results in corresponding rotation of gear (170) and shaft (172). Accordingly, when actuation mechanism (282) is activated to rotate, such rotation may be communicated via shafts (172, 284) and gears (170, 210) to effect rotation of manifold (144) as described above.

Figure 13:
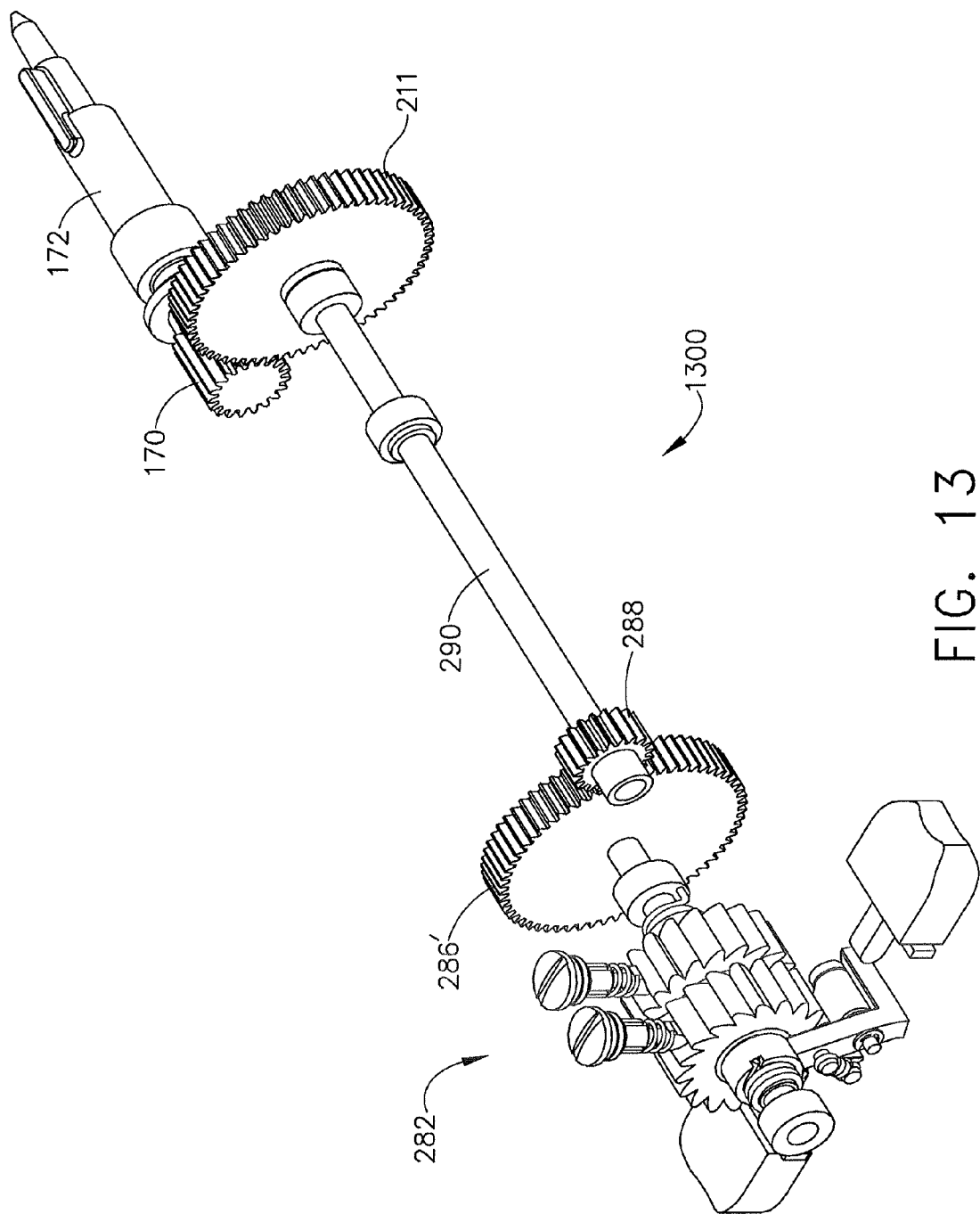
FIG. 13 depicts a perspective view of an alternate embodiment of a tissue sample holder rotation mechanism.
Figure 14:
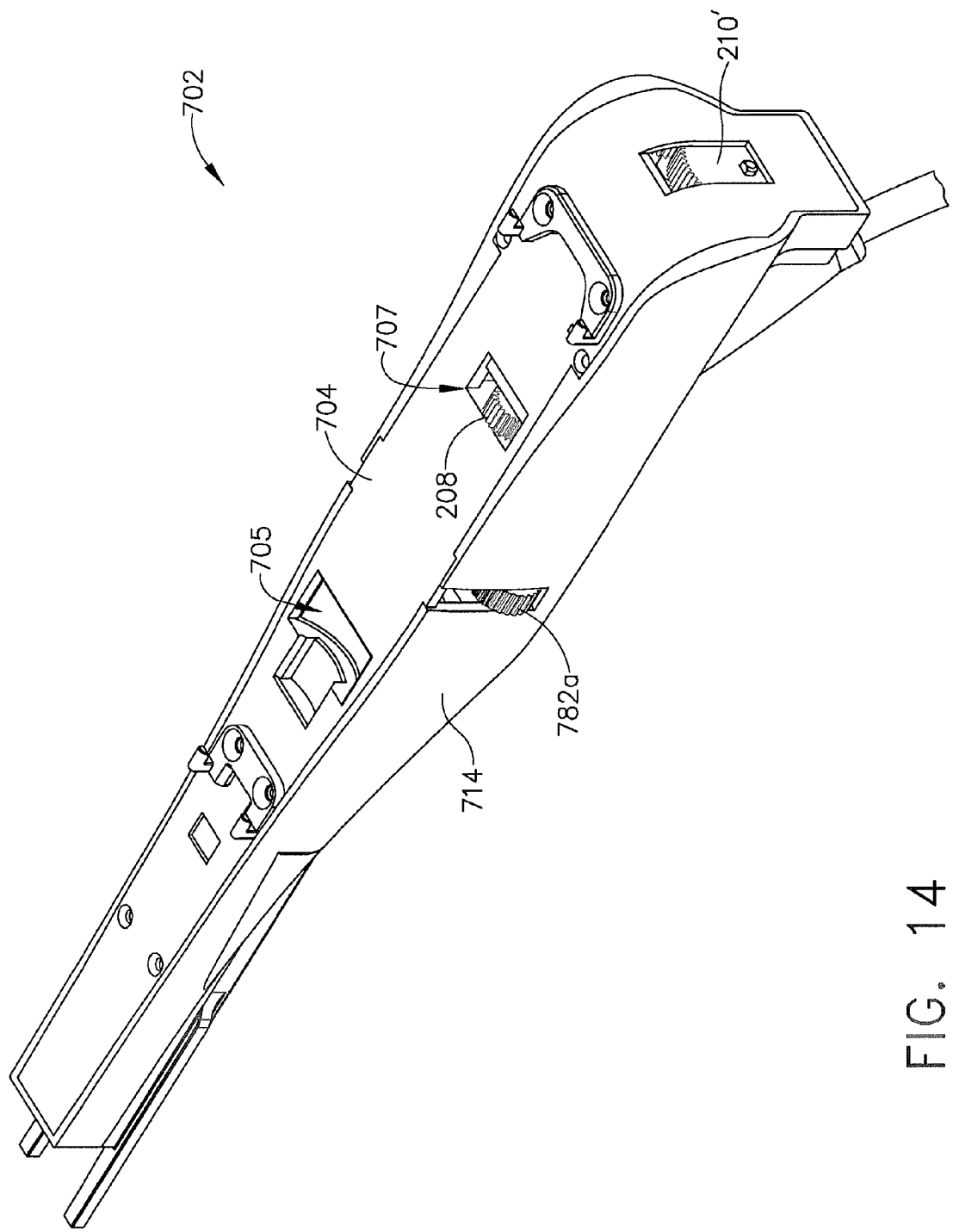
FIG. 14 depicts a perspective view of an exemplary alternate holster with an alternate tissue sample holder rotation mechanism.
Figure 15:
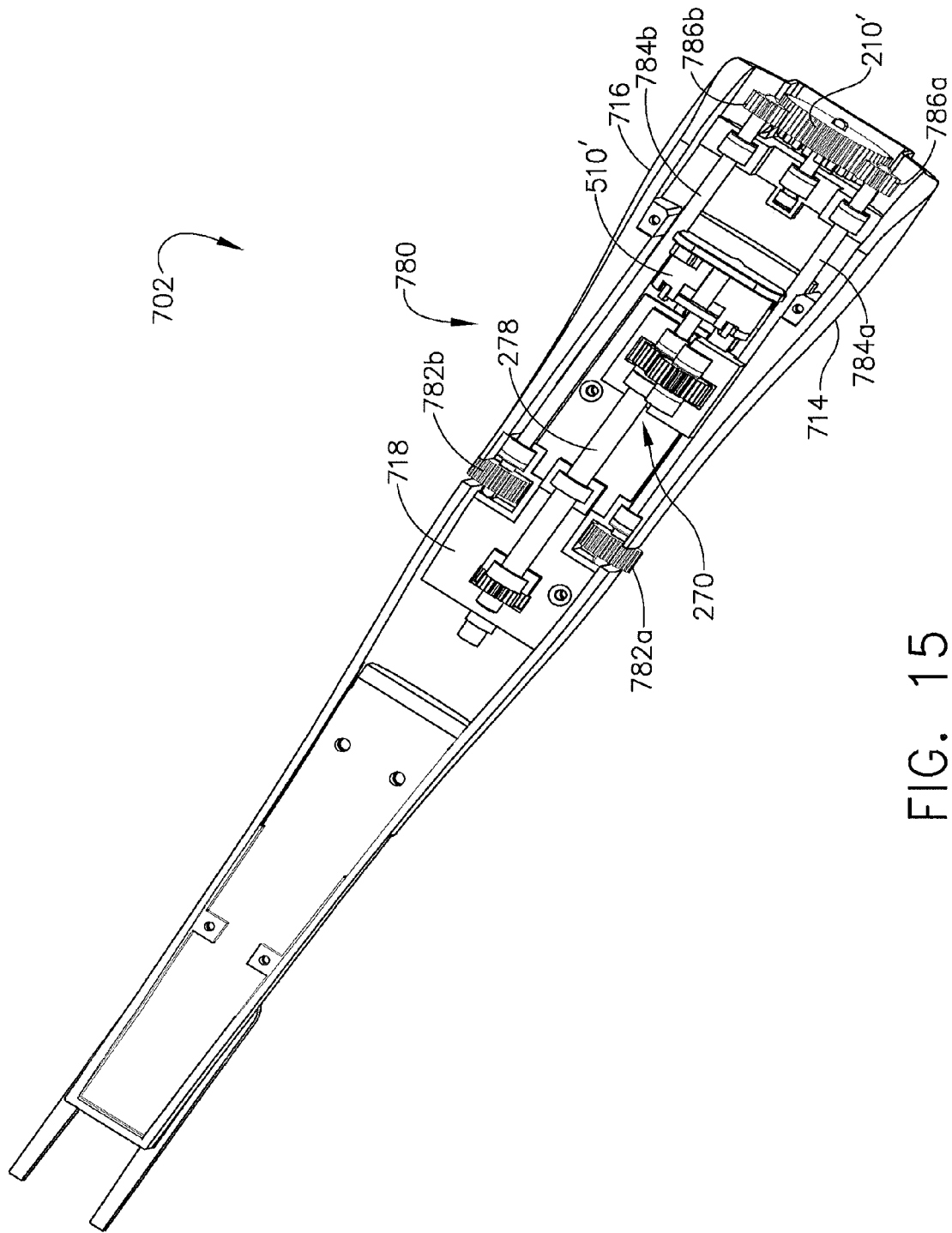
FIG. 15 depicts a top perspective view of the holster of FIG. 14, with some housing components omitted, showing a tissue sample holder rotation mechanism.
Figure 16:
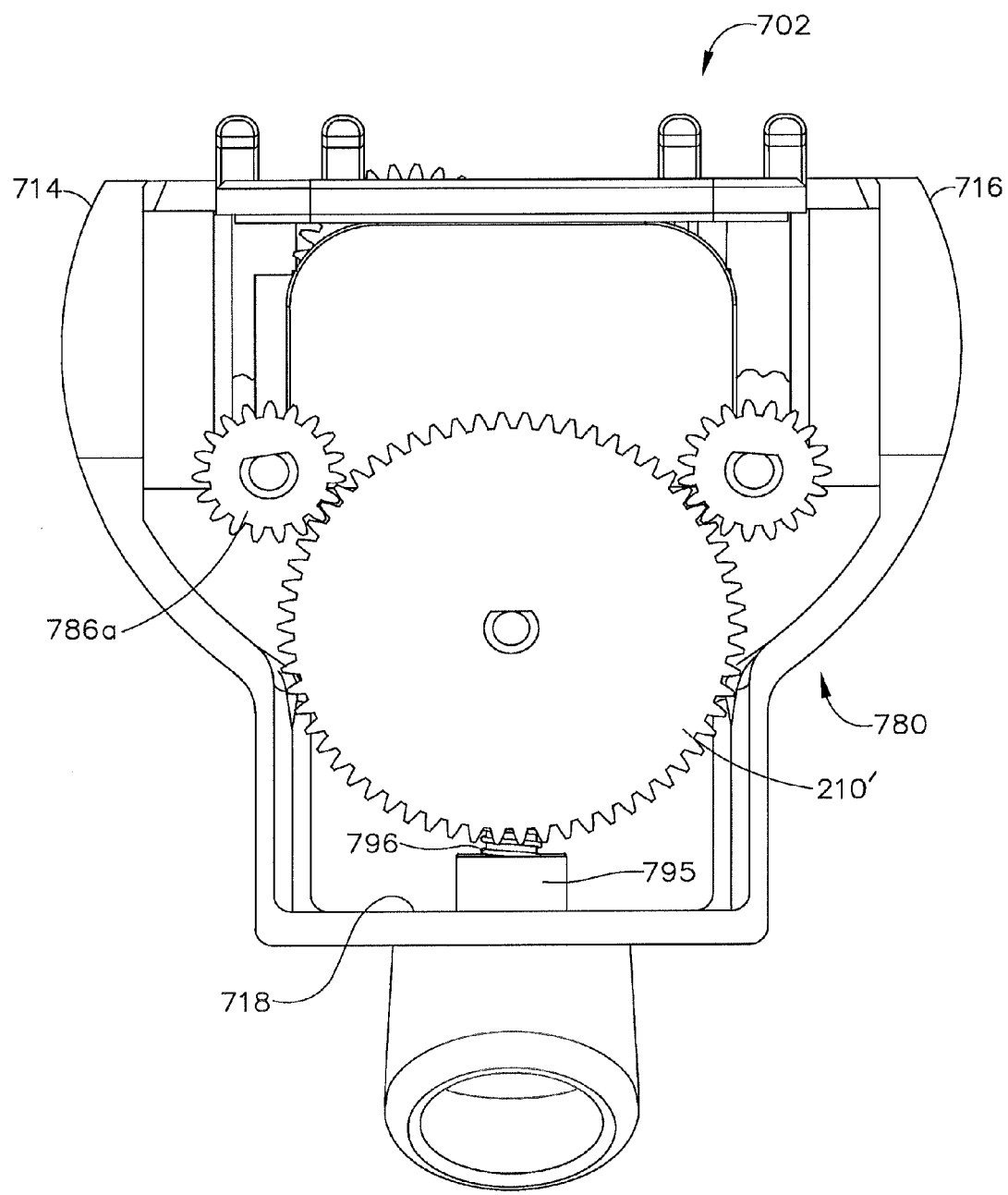
FIG. 16 depicts an end view of the holster of FIG. 14, with some housing components omitted.

Alternate structures and configurations may be used to communicate rotation from actuation mechanism (282) to manifold (144). By way of example only, one such alternate embodiment, which is simply a modified version of tissue sample holder rotation mechanism (280), is shown in FIG. 13. This modified mechanism may be used when it is desired to position actuation mechanism (282) distally further from the proximal end of probe (102) (e.g., to move actuation mechanism (282) closer to needle portion (10) and further from tissue sample holder (140)) or in any other circumstance. As shown in FIG. 13, the rotation generated by the actuation stroke is communicated from the actuation mechanism (282) to manifold (144) via gear train (1300). In this version, gear train (1300) comprises gears (211, 288) and extension shaft (290). Gear (286') is configured to mesh with gear (288), which is mounted toward the distal end of extension shaft (290). Gear (211), which has been noted above, is mounted toward the proximal end of extension shaft (290). In particular, gear (211) is configured to mesh with gear (170) of tissue sample holder (140) when biopsy probe (102) is coupled with holster (202). Of course, gears (211, 286', 288) may have any suitable number of teeth in order to provide an appropriate gear ratio. Accordingly, when actuation mechanism (282) is activated to rotate, such rotation may be communicated via shafts (172, 284', 290) and gears (170, 211, 286', 288), to effect rotation of manifold (144) as described above. Other ways in which a tissue holder rotation mechanism (280) may be configured or operated will be apparent to those of ordinary skill in the art in view of the teachings herein.

B. Side Thumbwheel Holster

FIGS. 14-17 depict an alternate holster embodiment that is capable of being coupled with probe (102) described above. In the illustrated version, side thumbwheel holster (702) is substantially identical to push button holster (202) described above, except that side thumbwheel holster (702) comprises an alternate tissue holder rotation mechanism (780). In particular, the cutter drive mechanism (270) of holster (702) is substantially identical to cutter drive mechanism (270) described above. However, in this example, encoder assembly (510') of holster (702) is mounted on the proximal end of idler shaft (278), while encoder assembly (510) of holster (202) is mounted on the distal end of idler shaft (278). In addition, similar to holster (202), top cover (704) of holster (702) comprises a recess (705) configured to receive a lower portion of center thumbwheel (74) when probe (102) and holster (702) are engaged. Top cover (704) further comprises opening (707) configured to expose gear (208) of cutter drive mechanism (270). As with holster (202), holster (702) may be of unitary or integral construction, or, alternatively, top cover (704), side panels (714, 716), and base member (718) may comprise individual components joined together using fasteners, such as screws, pins, or snap fittings, or any other suitable structures or techniques.

As shown, holster (702) is configured to be handheld, such that a biopsy device incorporating holster (702) may be manipulated and operated by a single hand of a user (e.g., using ultrasound guidance, etc.). However, it will be appreciated in view of the disclosure herein that holster (702) may be configured to be mounted to a table, fixture, or other device, such as for use in a stereotactic or X-ray setting, an MRI setting, or any other setting. As with holster (202) discussed above, holster (702) may be coupled with a targeting set, such as the targeting set disclosed in U.S. Non-Provisional patent application Ser. No. 12/337,872, entitled "MULTI-ORIENTATION TARGETING SET FOR MRI BIOPSY DEVICE," filed on even date herewith, the disclosure of which is incorporated by reference herein. Of course, it will be appreciated in view of the disclosure herein that holster (702) may be used in a variety of other settings and combinations.

1. Exemplary Tissue Holder Rotation Mechanism

As noted above, holster (702) comprises an alternate tissue holder rotation mechanism (780) configured to provide bi-directional manual indexing of tissue sample holder (140). Similar to tissue holder rotation mechanism (280) described above, tissue holder rotation mechanism (780) may be configured to be compatible for use in a magnetic environment by incorporating manually actuated mechanical components. As shown in FIGS. 14-17, tissue holder rotation mechanism (780) comprises two sets of indexing components, including a pair of side thumbwheels (782a, 782b), a pair of indexing shafts (784a, 784b), and a pair of indexing gears (786a, 786b). Each set of components is configured to allow users to rotate tissue sample holder (140) in both clockwise and counterclockwise directions. In an alternate embodiment (not shown), a holster may only include one side thumbwheel and corresponding set of components configured to provide bi-directional or unidirectional rotation of the tissue sample holder. Of course, other ways in which a tissue holder rotation mechanism (780) may be configured or operated will be apparent to those of ordinary skill in the art in view of the teachings herein.

In the illustrated version, side thumbwheels (782a, 782b) are positioned along and are partially exposed through side panels (714, 716). Side thumbwheels (782a, 782b) may be positioned such that when probe (102) and holster (702) are engaged, a user is able to rotate one of side thumbwheels (782a, 782b) while grasping the combined biopsy device with one hand. The dual thumbwheel configuration, as shown in FIGS. 14-17, also may permit a user to use either his/her right or left hand to grasp the biopsy device and index tissue sample holder (140) by rotating one of side thumbwheels (782a, 782b).

As shown in FIGS. 14-17, side thumbwheel (782a) is mounted adjacent to the distal end of indexing shaft (784a), while indexing gear (786a) is mounted adjacent to the proximal end of indexing shaft (784a). Side thumbwheel (782a), indexing shaft (784a), and indexing gear (786a) are configured to rotate unitarily with each other. Similarly, side thumbwheel (782b) is mounted adjacent to the distal end of indexing shaft (784b), while indexing gear (786b) is mounted adjacent to the proximal end of indexing shaft (784b). Side thumbwheel (782b), indexing shaft (784b), and indexing gear (786b) are also configured to rotate unitarily with each other. In the illustrated version, side thumbwheels (782a, 782b) rotate about central axes that are parallel to each other and parallel to the longitudinal axis of cutter (50). Indexing gears (786a, 786b) are configured to mesh with gear (210') such that indexing gears (786a, 786b) can impart rotation to gear (210').

In the illustrated embodiment, gear (210') comprises an inner face (212') which includes projections (213') on inner face (212'). Tissue holder rotation mechanism (780) further comprises a rotation restriction assembly (793) configured to provide at least nominal resistance to rotation of gear (210'). In this version, rotation restriction assembly (793) comprises pawl (794) mounted on a fixed shaft (795) and a compression spring (796). Pawl (794) is configured to releasably engage gear (210') via a single projection (213') and includes a cam profile configured to cause pawl (794) to travel vertically during rotation of gear (210'). Fixed shaft (795) is fixedly mounted to base member (718) of holster (702). As gear (210') rotates, a first projection (213'), which is initially engaged with pawl (794), forces pawl (794) vertically downward along fixed shaft (795) thereby compressing compression spring (796). After pawl (794) disengages first projection (213'), compression spring (796) urges pawl (794) vertically upward towards engagement with the next projection (213'). In this version, projections (213') are shaped like a teardrop, although any other suitable shape may be used.

Figure 17:
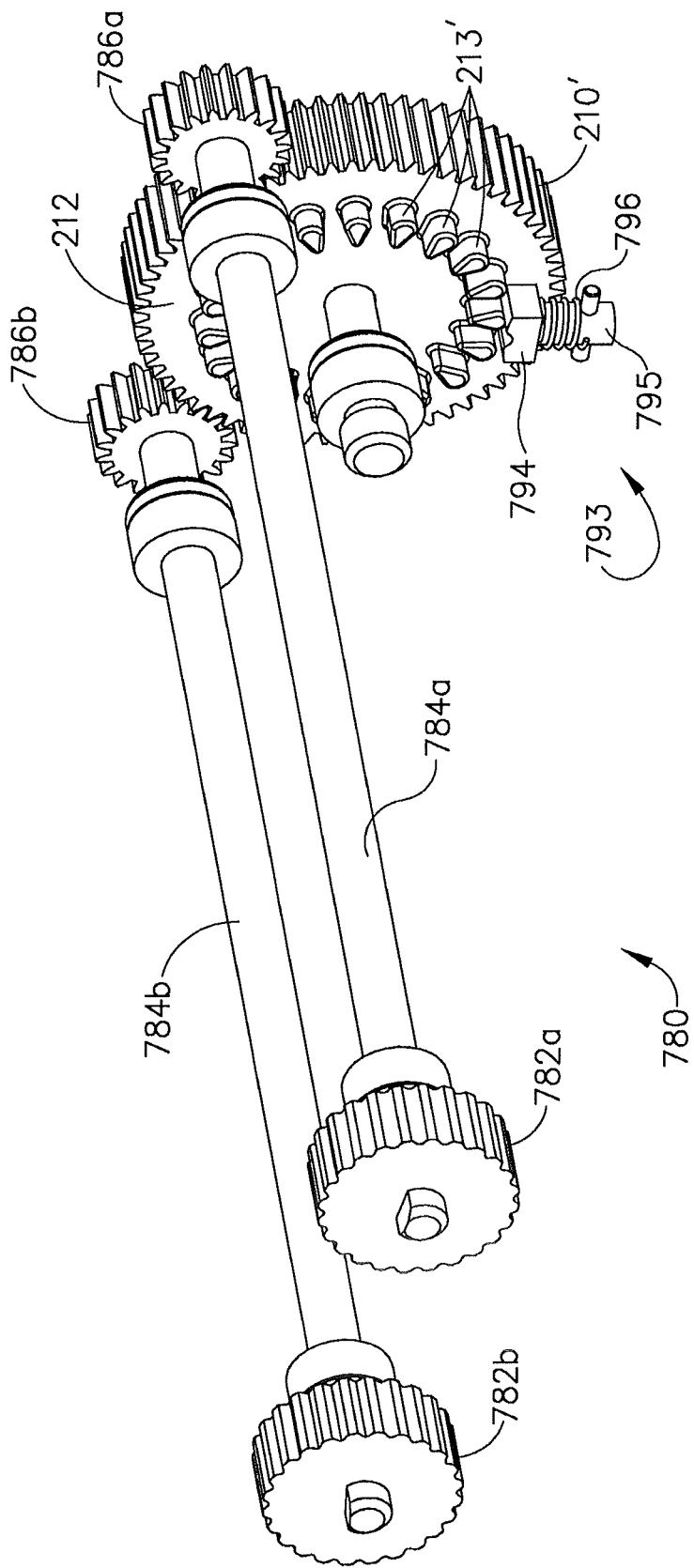
FIG. 17 depicts a perspective view of the tissue sample holder rotation mechanism of FIG. 15.

As shown in FIG. 17, gear (210') includes nineteen projections (213'), which corresponds to the number of chambers (150, 166) (including dedicated passage (158)) in tissue sample holder (140). The correlation between the number of projections (213') and the number of chambers (150, 166) in tissue sample holder (140) may facilitate rotation of gear (210') such that tissue sample holder (140) advances enough to align a consecutive chamber (150, 166) with cutter lumen (52). It should also be understood that rotation restriction assembly (793) may provide the operator with both tactile and audible feedback as the operator manipulates either thumbwheel (782a, 782b). For instance, the operator may be able to feel the interaction between pawl (794) and projection (213'), as communicated through either thumbwheel (782a, 782b). The operator may also be able to hear the interaction between pawl (794) and projection (213'), such as by a clicking or popping sound. Such feedback may indicate to the operator that the next chamber (150, 166) has been successfully indexed.

2. Exemplary Actuation Stroke

Tissue holder rotation mechanism (780) depicted in FIGS. 14-17 is configured to index tissue holder (140) one chamber (150, 166) during a single actuation stroke, thereby allowing a user to align successive chambers (150, 166) with cutter lumen (52) to receive successive tissue samples (4). This functionality may facilitate collection of multiple tissue samples (4) without requiring the user to remove the biopsy device from the patient. Of course, tissue holder rotation mechanism (780) may be configured to index tissue holder (140) any suitable number of chambers (150, 166) during a single actuation stroke.

In the illustrated embodiment, an actuation stroke producing rotation of manifold (144) may be induced by rotating one of side thumbwheels (782a, 782b). As noted above, side thumbwheel (782a), indexing shaft (784a), and indexing gear (786a) are configured to rotate unitarily. Similarly, side thumbwheel (782b), indexing shaft (784b), and indexing gear (786b) are also configured to rotate unitarily. Indexing gears (786a, 786b) are configured to mesh with gear (210'). As a result, the rotation generated by the actuation stroke is communicated from side thumbwheel (782a, 782b) to gear (210') via indexing shaft (784a, 784b) and indexing gear (786a, 786b). As discussed above, rotation of gear (210') may be partially restrained by pawl (794) which travels vertically during rotation of gear (210'), disengaging a first projection (213') and re-engaging a second projection (213').

Similar to gear (210), in the version shown in FIGS. 14-17, gear (210') is configured to be at least partially exposed through the proximal surface of top cover (704) and to mesh with gear (170) of tissue sample holder (140) when biopsy probe (102) is coupled with holster (702). When probe (102) and holster (702) are engaged, rotation of gear (210') results in corresponding rotation of gear (170) and shaft (172). Accordingly, when tissue rotation mechanism (780) is activated to rotate, such rotation may be communicated via shafts (172, 784a, 784b) and gears (170, 210', 786a, 786b) to effect rotation of manifold (144) as described above. Of course, any other suitable structures and configurations may be used to communicate rotation from tissue rotation mechanism (780) to manifold (144).

C. Worm Drive Holster

Figure 18:
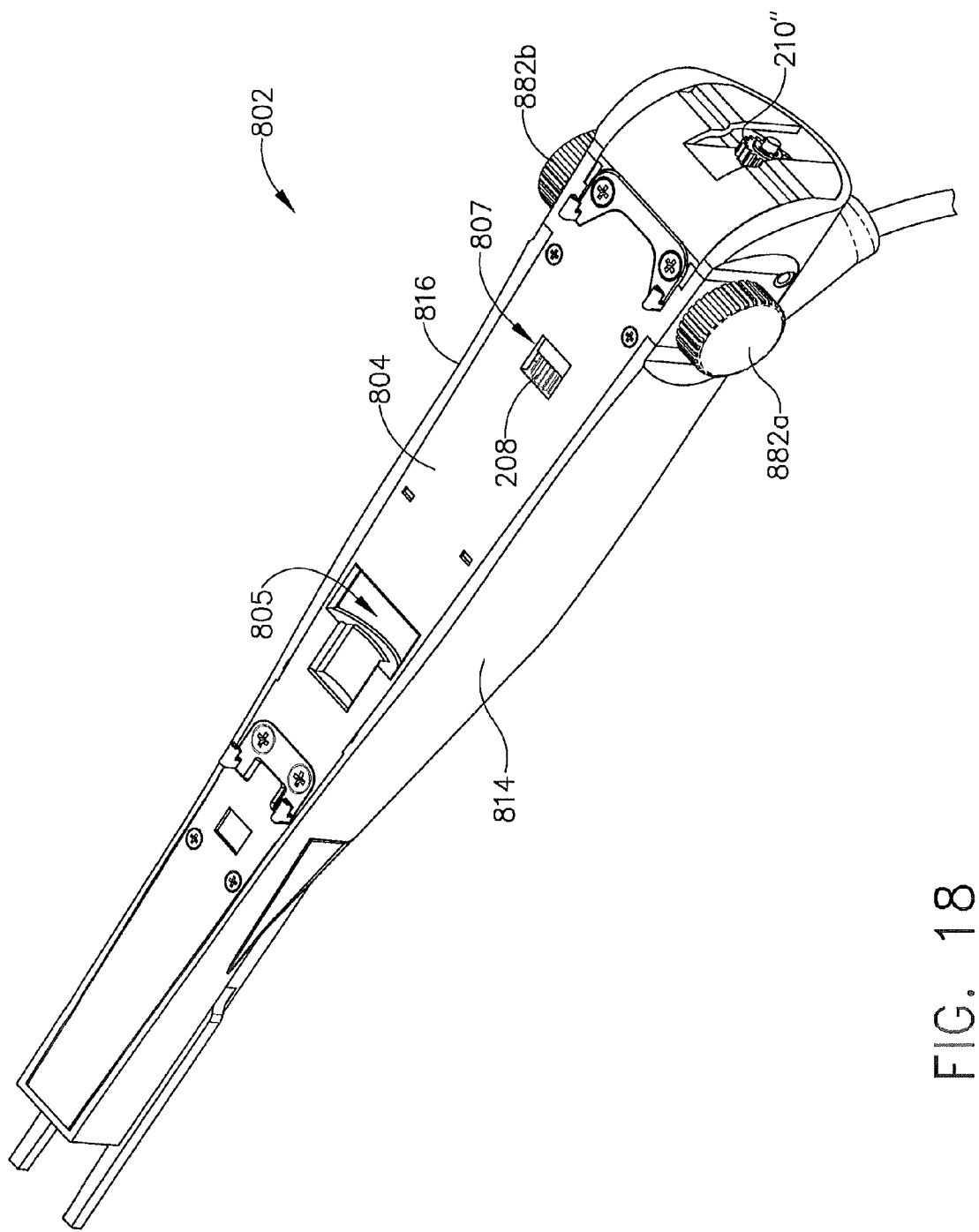
FIG. 18 depicts a perspective view of another exemplary alternate holster.
Figure 19:
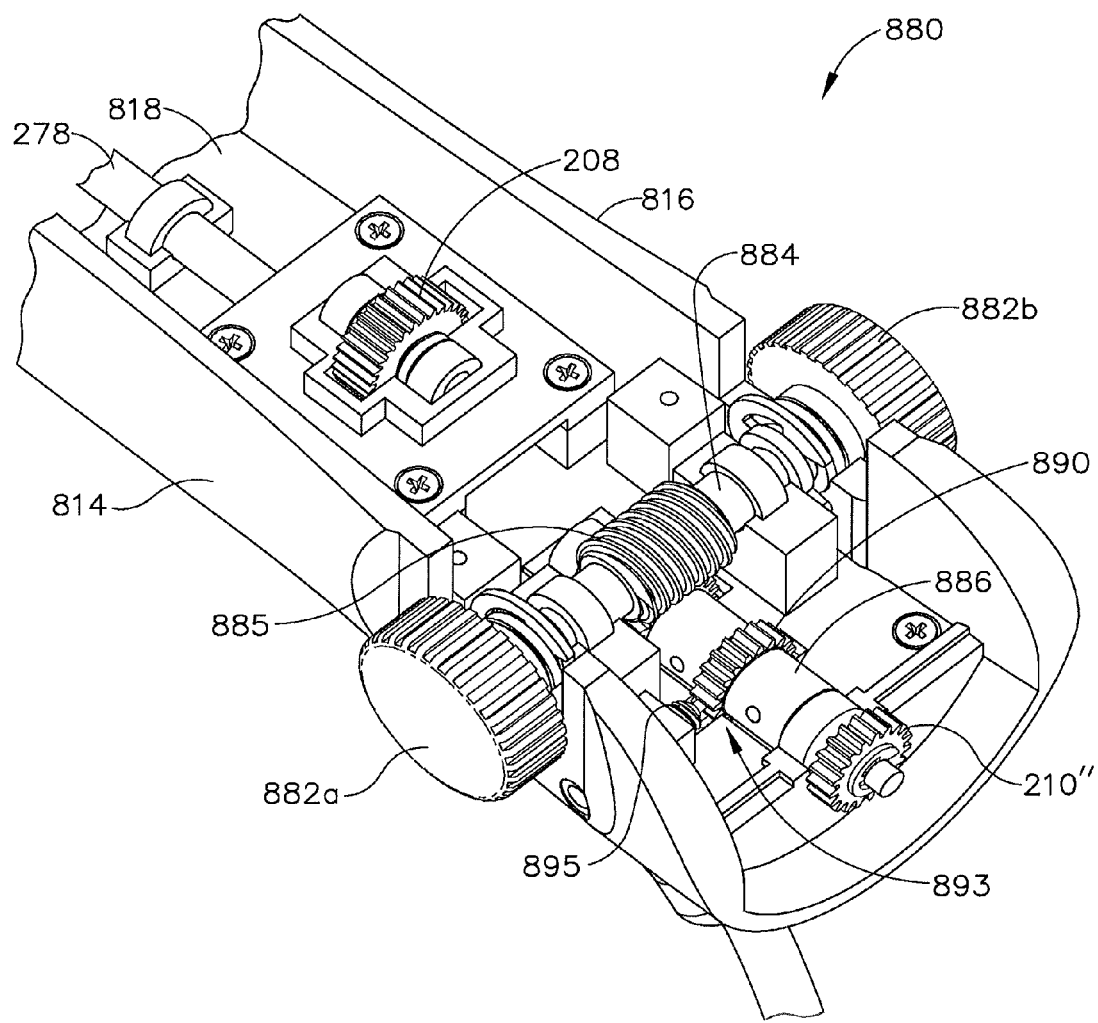
FIG. 19 depicts a partial perspective view of the holster of FIG. 18, with some housing components omitted, showing a tissue sample holder rotation mechanism.
Figure 20:
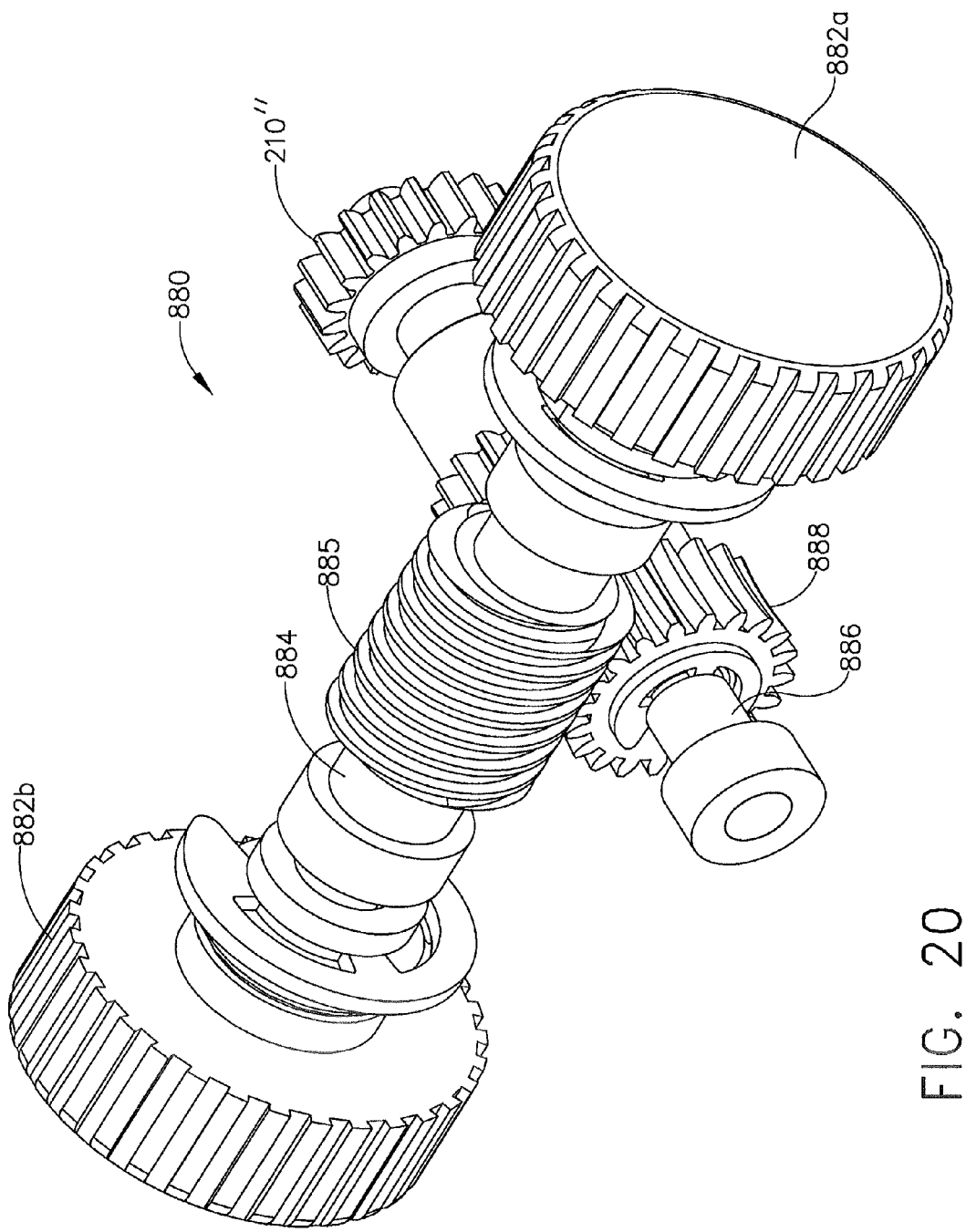
FIG. 20 depicts a perspective view of the tissue sample holder rotation mechanism of FIG. 19.

FIGS. 18-20 depict an alternate holster embodiment that is capable of being coupled with probe (102) described above. In the illustrated version, worm drive holster (802) is substantially identical to push button holster (202) described above, except that worm drive holster (802) comprises an alternate tissue holder rotation mechanism (880). In particular, the cutter drive mechanism (not fully shown) of holster (802) is substantially identical to cutter drive mechanism (270) described above. In addition, similar to holster (202), top cover (804) of holster (802) comprises a recess (805) configured to receive a lower portion of center thumbwheel (74) when probe (102) and holster (802) are engaged. Top cover (804) further comprises opening (807) configured to expose gear (208) of cutter drive mechanism (not fully shown). As with holster (202), holster (802) may be of unitary or integral construction, or, alternatively, top cover (804), side panels (814, 816), and base member (818) may comprise individual components joined together using fasteners, such as screws or pins, or any other suitable structures or techniques.

As shown, holster (802) is configured to be handheld. However, it will be appreciated in view of the disclosure herein that holster (802) may be configured to be mounted to a table, fixture, or other device, such as for use in a stereotactic or X-ray setting, an MRI setting, PEM setting, BSGI setting, or any other setting. As with holster (202) discussed above, holster (802) may be coupled with a targeting set, such as the targeting set disclosed in U.S. Non-Provisional patent application Ser. No. 12/337,872, entitled "MULTI-ORIENTATION TARGETING SET FOR MRI BIOPSY DEVICE," filed on even date herewith, the disclosure of which is incorporated by reference herein. Of course, it will be appreciated in view of the disclosure herein that holster (802) may be used in a variety of other settings and combinations.

1. Exemplary Tissue Holder Rotation Mechanism

As noted above, holster (802) comprises an alternate tissue holder rotation mechanism (880) configured to provide bi-directional manual indexing of tissue sample holder (140). Similar to tissue holder rotation mechanisms (280, 780) described above, tissue holder rotation mechanism (880) may be configured to be compatible for use in a magnetic environment by incorporating manually actuated mechanical components. As shown in FIGS. 18-20, tissue holder rotation mechanism (880) comprises a pair of side thumbwheels (882a, 882b) coaxially mounted to opposite ends of a worm shaft (884) such that side thumbwheels (882a, 882b) and worm shaft (884) rotate unitarily. Side thumbwheels (882a, 882b) rotate about a common axis that is perpendicular to the longitudinal axis of cutter (50). Each side thumbwheel (882a, 882b) is configured to allow a user to rotate tissue sample holder (140) in both clockwise and counterclockwise directions. Tissue holder rotation mechanism (880) further comprises an indexing shaft (886) and gears (210", 888, 890), which are coaxially mounted along indexing shaft (886) such that indexing shaft (886) and gears (210", 888, 890) rotate unitarily. Gear (210") may comprise a hubless gear, although this is not required. In an alternate embodiment (not shown), a holster may only include one side thumbwheel and corresponding set of components configured to provide bi-directional or uni-directional rotation of the tissue sample holder. Of course, other ways in which a tissue holder rotation mechanism (880) may be configured or operated will be apparent to those of ordinary skill in the art in view of the teachings herein.

In the illustrated version, side thumbwheels (882a, 882b) are positioned along and protrude through side panels (814, 816). Side thumbwheels (882a, 882b) may be positioned such that when probe (102) and holster (802) are engaged, a user is able to rotate one of side thumbwheels (882a, 882b) while grasping the combined biopsy device with one hand. The dual thumbwheel configuration, as shown in FIGS. 18-20, also may permit a user to use either his/her right or left hand to grasp the biopsy device and index tissue sample holder (140) by rotating one of side thumbwheels (882a, 882b).

As shown in FIGS. 18-20, side thumbwheels (882a, 882b) are coaxially mounted to opposite ends of worm shaft (884) such that side thumbwheels (882a, 882b) and worm shaft (884) rotate unitarily. Worm shaft (884) includes worm threading (885) positioned along a central portion of worm shaft (884). Worm threading (885) may have any suitable orientation, including either a right hand or a left hand orientation. In the illustrated version, worm gear (888) meshes with worm threading (885) such that worm shaft (884) can impart rotation to worm gear (888), and, subsequently, to gears (210", 890) and indexing shaft (886). As shown, tissue holder rotation mechanism (880) further comprises a rotation restriction assembly (893) configured to provide at least nominal resistance to rotation of gears (210", 888, 890) in order to facilitate indexing of tissue holder (140) one chamber (150, 166) at a time. Of course, like other components described herein, a rotation restriction assembly is merely optional.

In this embodiment, gears (210", 888, 890) include nineteen teeth, which corresponds to the number of chambers (150, 166) (including dedicated passage (158)) in the tissue sample holder (140). The correlation between the number of teeth on gears (210", 888, 890) and the number of chambers (150, 166) in the tissue sample holder (140) may help limit indexing of tissue sample holder (140) to one chamber (150) at a time. However, this is not required. Gears (210", 888, 890) may comprise any suitable number of teeth.

In this version, rotation restriction assembly (893) comprises restrictor (895) configured to releasably engage the teeth on gear (890) thereby at least partially restricting rotation of gears (210", 888, 890). It should also be understood that rotation restriction assembly (893) may provide the operator with both tactile and audible feedback as the operator manipulates either thumbwheel (882a, 882b). For instance, the operator may be able to feel the interaction between restrictor (895) and teeth on gear (890), as communicated through either thumbwheel (882a, 882b). The operator may also be able to hear the interaction between restrictor (895) and teeth on gear (890), such as by a clicking or popping sound. Such feedback may indicate to the operator that the next chamber (150, 166) has been successfully indexed.

2. Exemplary Actuation Stroke

Tissue holder rotation mechanism (880) depicted in FIGS. 18-20 is configured to index tissue holder (140) one chamber (150, 166) during a single actuation stroke, thereby allowing a user to align successive chambers (150, 166) with cutter lumen (52) to receive successive tissue samples (4). This functionality may facilitate collection of multiple tissue samples (4) without requiring the user to remove the biopsy device from the patient. Of course, tissue holder rotation mechanism (880) may be configured to index tissue holder (140) any suitable number of chambers (150, 166) during a single actuation stroke.

In the illustrated version, an actuation stroke producing rotation of manifold (144) may be induced by rotating one of side thumbwheels (882a, 882b). As noted above, side thumbwheels (882a, 882b) and worm shaft (884) are configured to rotate unitarily. Worm threading (885) is configured to mesh with worm gear (888). As a result, the rotation generated by the actuation stroke is communicated from side thumbwheel (882a, 882b) to gear (210") via worm shaft (884), indexing shaft (886) and worm gear (888). As discussed above, rotation of gear (890), and consequently gear (210") may be partially restricted by restrictor (895).

Similar to gear (210), in the version shown in FIGS. 18-20, gear (210") is configured to be at least partially exposed through the proximal surface of top cover (804) and to mesh with gear (170) of tissue sample holder (140) when biopsy probe (102) is coupled with holster (802). When probe (102) and holster (802) are engaged, rotation of gear (210") results in corresponding rotation of gear (170) and shaft (172). Accordingly, when tissue rotation mechanism (880) is activated to rotate, such rotation may be communicated via shafts (172, 886), worm shaft (884), and gears (170, 210", 888, 890) to effect rotation of manifold (144) as described above. Of course, any other suitable structures and configurations may be used to communicate rotation from tissue rotation mechanism (880) to manifold (144).

III. Combined Cutter Biopsy Device

FIGS. 21-26 depict an alternate embodiment of a biopsy device (1000). As shown, combined cutter biopsy device (1000) is formed when probe (1102) is coupled with holster (1202). Similar to biopsy device (100), biopsy device (1000) is configured to sever a targeted tissue sample (4) and transfer tissue sample (4) into a tissue sample holder (140'). Tissue sample holder (140') is attached to probe (1102) and is substantially similar to tissue sample holder (140) described above. For instance, tissue sample holder (140') may be configured in accordance with any of the teachings of U.S. Pub. No. 2008/0195066, entitled "Revolving Tissue Sample Holder For Biopsy Device," published Aug. 14, 2008, the disclosure of which is incorporated by reference herein. Alternatively, tissue sample holder (140') may be configured in accordance with any of the teachings of U.S. Non-Provisional patent application Ser. No. 12/337,911, entitled "BIOPSY DEVICE WITH DISCRETE TISSUE CHAMBERS," filed on even date herewith, the disclosure of which is incorporated by reference herein. Of course, any other suitable structures or configurations for tissue sample holder (140, 140') or manifold (144) may be used.

A. Combined Cutter Holster

In the illustrated embodiment, holster (1202) comprises a top cover (1204), through which a portion of gear (208) is exposed, side panels (1214, 1216), and a base member (1218). Holster (1202) may be of unitary or integral construction, or, alternatively, top cover (1204), side panels (1214, 1216), and base member (1218) may comprise individual components joined together using fasteners, such as screws or pins, or any other suitable structures or techniques. Holster (1202) of this example further comprises a cutter drive mechanism (not shown). Various other components, features, and methods of operation for holster (1202) are described in greater detail in U.S. Non-Provisional patent application Ser. No. 12/337,674, entitled "BIOPSY DEVICE WITH SLIDING CUTTER COVER," filed on even date herewith, the disclosure of which is incorporated by reference herein. Indeed, probe (1102) and/or holster (1202) may be configured in accordance with any of the teachings of U.S. Non-Provisional patent application Ser. No. 12/337,674, entitled "BIOPSY DEVICE WITH SLIDING CUTTER COVER," filed on even date herewith, the disclosure of which is incorporated by reference herein.

As shown, holster (1202) is configured to be handheld. However, it will be appreciated in view of the disclosure herein that holster (1202) may be configured to be mounted to a table, fixture, or other device, such as for use in a stereotactic or X-ray setting, an MRI setting, PEM setting, BSGI setting, or any other setting. As with holster (202) discussed above, holster (1202) may be coupled with a targeting set, such as the targeting set disclosed in U.S. Non-Provisional patent application Ser. No. 12/337,872, entitled "MULTI-ORIENTATION TARGETING SET FOR MRI BIOPSY DEVICE," filed on even date herewith, the disclosure of which is incorporated by reference herein. Of course, it will be appreciated in view of the disclosure herein that holster (1202) may be used in a variety of other settings and combinations.

B. Combined Cutter Probe

FIGS. 21-24 depict an exemplary embodiment of a probe (1102) that is configured to be coupled with holster (1202). In the illustrated version, probe (1102) comprises a cutter portion (1110) and a body portion (1112). Body portion (1112) comprises a cover member (1114) and a base member (1116). Probe (1102) also includes a hollow cutter (50) that is operable to sever and communicate tissue samples as described above with respect to probe (102). A tissue sample holder (140') is removably secured to base member (1116), though tissue sample holder (140') may alternatively be secured to cover member (1114) or some other component. Tissue sample holder (140') comprises a cup (142'), a manifold (144') and trays (160'), among other components. Trays (160') define separate tissue sample chambers (166'), which may be successively aligned with cutter lumen (52) through rotation of manifold (144'). It should therefore be understood that manifold (144') may be rotated to index tissue sample chambers (166') to cutter lumen (52), such as to receive tissue samples captured by cutter (50) and communicated proximally through cutter lumen (52) to tissue sample chambers (166').

In the present example, tissue sample holder (140') and its components are substantially similar to tissue sample holder (140) and the components described above and further described in U.S. Pub. No. 2008/0195066, entitled "Revolving Tissue Sample Holder For Biopsy Device," published Aug. 14, 2008, the disclosure of which is incorporated by reference herein. Alternatively, tissue sample holder (140') may be configured in accordance with any of the teachings of U.S. Non-Provisional patent application Ser. No. 12/337,911, entitled "BIOPSY DEVICE WITH DISCRETE TISSUE CHAMBERS," filed on even date herewith, the disclosure of which is incorporated by reference herein. Of course, any other suitable structures or configurations for tissue sample holder (140') may be used.

Various other components, features, and methods of operation for probe (1102) are described in greater detail in U.S. Non-Provisional patent application Ser. No. 12/337,674, entitled "BIOPSY DEVICE WITH SLIDING CUTTER COVER," filed on even date herewith, the disclosure of which is incorporated by reference herein.

Probe (1102) further comprises tissue holder rotation mechanism (1180), which will be discussed in more detail below.

1. Exemplary Tissue Holder Rotation Mechanism

In contrast to tissue holder rotation mechanisms (280, 780, 880) described above, which were contained within holsters (202, 702, 802), tissue holder rotation mechanism (1180) is incorporated into probe (1102). It should be understood, however, that tissue holder rotation mechanisms (280, 780, 880) could be incorporated into probe (102, 1102) instead of holsters (202, 702, 802), if desired. Likewise, tissue holder rotation mechanism (1180) may be incorporated into holster (1202), if desired. Similar to tissue holder rotation mechanisms (280, 780, 880) described above, tissue holder rotation mechanism (1180) may be configured to be compatible for use in a magnetic environment by incorporating manually actuated mechanical components. As shown in FIGS. 21-26, tissue holder rotation mechanism (1180) comprises a ratcheting lever (1182), a ratchet (1184), a rotation restriction assembly (1190), and an indexing shaft (172'). In this version, tissue holder rotation mechanism (1180) is configured to provide uni-directional manual indexing of tissue sample holder (140'). Of course, other ways in which a tissue holder rotation mechanism (1180) may be configured or operated will be apparent to those of ordinary skill in the art in view of the teachings herein.

In the illustrated version, ratcheting lever (1182) is positioned toward the proximal portion of biopsy device (1000) and extends through an opening in cover member (1114). Ratcheting lever (1182) may be positioned such that when probe (1102) and holster (1202) are engaged, a user is able to depress ratcheting lever (1182) and initiate an actuation stroke while grasping biopsy device (1000) with one hand. During an actuation stroke, a user depresses ratcheting lever (1182) which causes tissue sample holder (140') to rotate and advance by one chamber (150', 166') and selectively align a consecutive chamber (150', 166') with cutter lumen (52). The actuation stroke will be discussed in more detail below.

Figure 25:
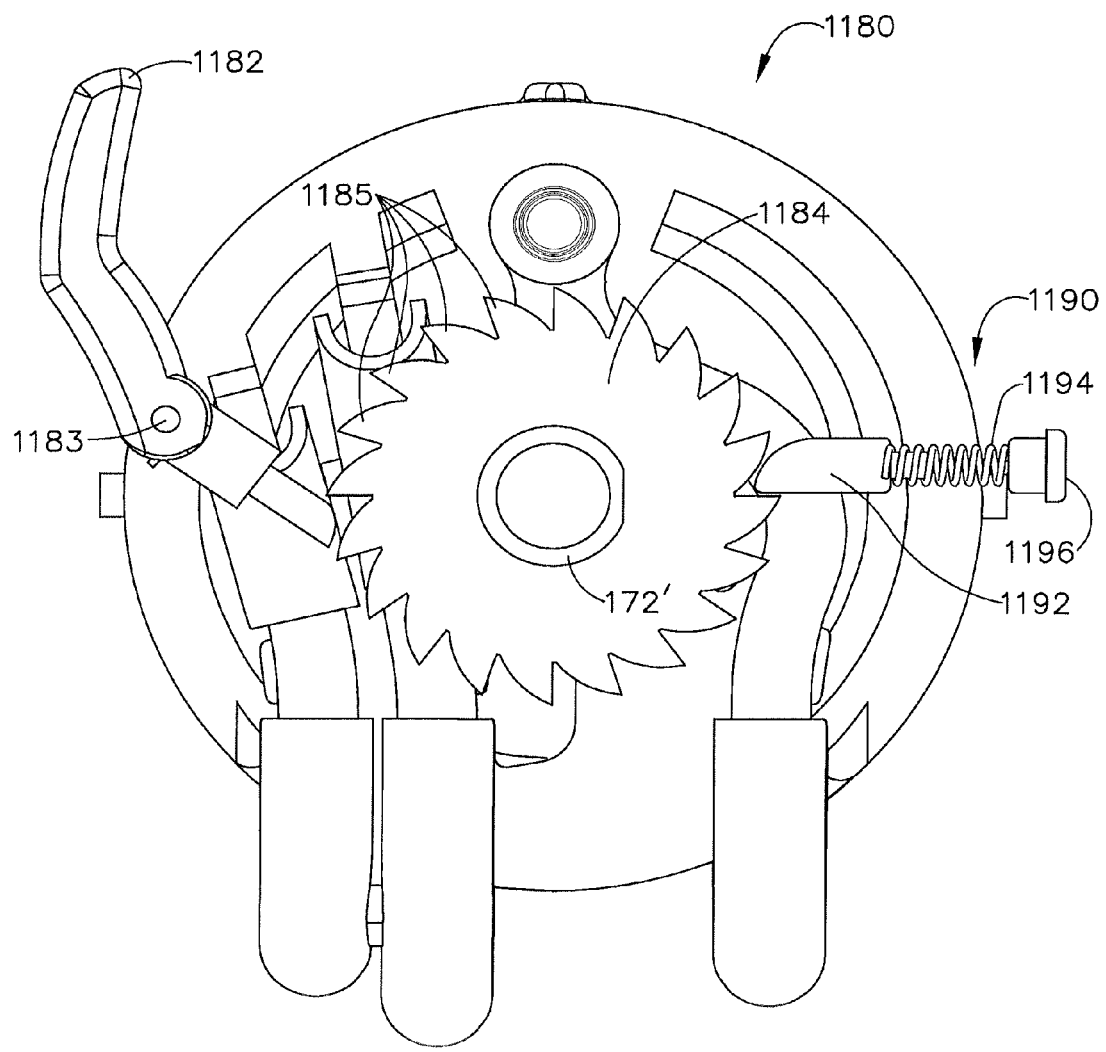
FIG. 25 depicts an end view of a tissue sample holder rotation mechanism of the probe of FIG. 23.
Figure 26:
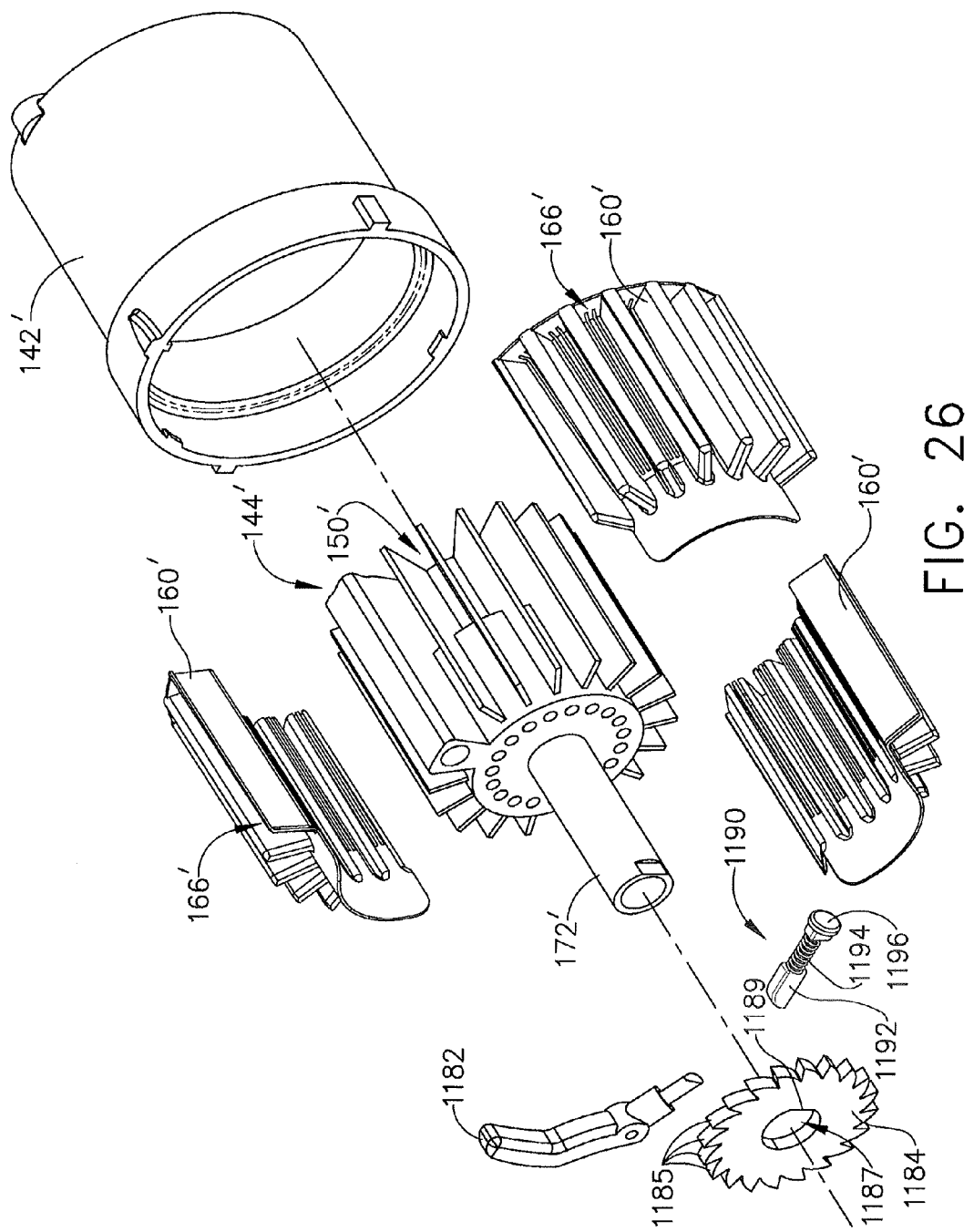
FIG. 26 depicts an exploded view of the tissue sample holder rotation mechanism of FIG. 25 and a tissue sample holder of the probe of FIG. 23.

As shown in FIGS. 25-26, ratcheting lever (1182) is configured to engage ratchet (1184), as ratcheting lever (1182) is depressed, by contacting one of the plurality of teeth (1185) positioned along the outer circumference of ratchet (1184), thereby urging ratchet (1184) to rotate in a clockwise direction. In this version, ratcheting lever (1182) pivots about pin (1183) which is formed as an integral projection of cover member (1114). Of course other suitable structures or devices to allow ratcheting lever (1182) to pivot may be used. A torsion spring (not shown) is also in mechanical communication with ratcheting lever (1182), and the torsion spring (not shown) is configured to urge ratcheting lever (1182) toward its starting position (e.g., disengaged from ratchet (1184)) upon completion of an actuation stroke.

In the illustrated version, rotation restriction assembly (1190) is positioned diametrically across from the point where ratcheting lever (1182) engages ratchet (1184). Of course, other suitable positions along the circumference of ratchet (1184) and orientations for rotation restriction assembly (1190) will be apparent to those of ordinary skill in the art in view of the teachings herein. As shown, rotation restriction assembly (1190) comprises a reciprocating pawl (1192), a compression spring (1194) and a cap (1196). Rotation restriction assembly (1190) is configured to allow ratchet (1184) to rotate in one direction (i.e. clock-wise in the illustrated version), while preventing ratchet (1184) from rotating in the reverse direction. Of course, this orientation may be reversed in alternate embodiments.

In the illustrated example, cap (1186) is configured to be attached to cover member (1114) and to allow pawl (1192) to travel horizontally during clock-wise rotation of ratchet (1184). Compression spring (1194) is positioned between cap (1196) on an outer end and pawl (1192) on an inner end. As shown in FIGS. 25-26, pawl (1192) releasably engages one of the plurality of teeth (1185) of ratchet (1184) and includes a cam profile configured to cause pawl (1192) to travel horizontally during clock-wise rotation of ratchet (1184). Compression spring (1194) may be configured to allow pawl (1192) to travel horizontally outward during clockwise rotation of ratchet (1184), while concomitantly urging pawl (1192) inward toward re-engagement with ratchet (1184).

In the present example, ratchet (1184) comprises a plurality of teeth (1185) along the circumference of ratchet (1184) and a central opening (1187). The number of teeth (1185) may or may not correspond directly or indirectly with the number of chambers (166) of tissue sample holder (140'). Central opening (1187) may be configured to engage shaft (172') such that ratchet (1184) and shaft (172') rotate unitarily. In this particular example, central opening (1187) includes a flat (1189) configured to engage a corresponding flat on shaft (172'). Of course other suitable structures or devices to ensure engagement between ratchet (1184) and shaft (172') may be used. In the illustrated version, while shaft (172') engages ratchet (1184) at a first end, as described above, shaft (172') is also configured to engage manifold (144') at the opposite end. In particular, shaft (172') is configured to engage a central recess in manifold (144') such that shaft (172') and manifold (144') rotate unitarily (e.g., through a key-keyway relationship, hex fitting, etc.). Shaft (172') may be integral with manifold (144') or be engaged therewith using any other suitable structure or configuration.

2. Exemplary Actuation Stroke

Tissue holder rotation mechanism (1180) depicted in FIGS. 21-26 is configured to index tissue holder (140') one chamber (150', 166') during a single actuation stroke, thereby allowing a user to align successive chambers (150', 166') with cutter lumen (52) to receive successive tissue samples (4). This functionality may facilitate collection of multiple tissue samples (4) without requiring the user to remove biopsy device (1000) from the patient. Of course, tissue holder rotation mechanism (1180) may be configured to index tissue holder (140') any suitable number of chambers (150', 166') during a single actuation stroke.

In the illustrated embodiment, an actuation stroke may be induced by depressing ratcheting lever (1182), which causes ratcheting lever (1182) to pivot about pin (1183) and engage one of the plurality of teeth (1185) of ratchet (1184). Upon engaging ratchet (1184), the pivoting action of ratcheting lever (1182) urges ratchet (1184) to rotate in a clockwise direction. As ratchet (1184) rotates, pawl (1192), which is engaged with a tooth (1185) on ratchet (1184) is forced horizontally outward by the tooth (1185), thereby compressing compression spring (1194). As ratchet (1184) continues to rotate, the first tooth (1185) disengages from pawl (1192) and pawl (1192) is urged horizontally inward by compression spring (1194) to engage the successive tooth (1185) on ratchet (1184). The re-engagement of ratchet (1184) by pawl (1192) prevents reverse rotation of ratchet (1184).

Simultaneously, the rotation of ratchet (1184) is translated to shaft (172') because those two components rotate unitarily. The rotation generated by the actuation stroke is communicated from the tissue holder rotation mechanism (1180) to manifold (144') via shaft (172'). As noted above, shaft (172') and manifold (144') are engaged such that they rotate unitarily. Accordingly, as tissue holder rotation mechanism (1180) is activated to rotate, ratchet (1184), shaft (172'), and manifold (144') all rotate unitarily, thereby resulting in the indexing of tissue sample holder (140') as described above with regard to tissue sample holder (140) and manifold (144). Of course, alternate structures and configurations may be used to communicate rotation from the tissue holder rotation mechanism (1180) to manifold (144').

It should also be understood that rotation restriction assembly (1190) may provide the operator with both tactile and audible feedback as the operator manipulates ratcheting lever (1182). For instance, the operator may be able to feel the interaction between pawl (1192) and teeth (1185), as communicated through ratcheting lever (1182). The operator may also be able to hear the interaction between pawl (1192) and teeth (1185), such as by a clicking or popping sound. Such feedback may indicate to the operator that the next chamber (166') has been successfully indexed.

III. Exemplary Vacuum Control Module and Canister

As shown in FIG. 1, an exemplary vacuum canister (401) is configured to be coupled vacuum control module (400). Vacuum control module (400) is operable to induce a vacuum through vacuum canister (401), and such a vacuum may be communicated to biopsy probe (102). For instance, vacuum control module (400) may communicate a vacuum through tube (404), which may then communicate the vacuum through tissue sample holder (140) to cutter lumen (52) as described above. Vacuum control module (400) may also communicate a vacuum through tube (402) to a manifold that is coupled with outer cannula (12), which may then communicate the vacuum to vacuum lumen (40) as described above.

Furthermore, vacuum canister (401) is operable to collect fluids that are communicated from biopsy probe (102) during use of biopsy probe (102). Vacuum canister (401) may thus be regarded as providing a fluid interface between biopsy probe (102) and vacuum control module (400). Any suitable vacuum control module and vacuum canister may be used such as those described in U.S. Pub. No. 2008/0195066, entitled "Revolving Tissue Sample Holder For Biopsy Device," published Aug. 14, 2008, the disclosure of which is incorporated by reference herein. Further, any other suitable component, system, technique, or device may be used with the suitable control module or vacuum canister.

Vacuum control module (400) of the present example also includes a motor (403) operable to control at least some components of holster (202). For instance, motor (403) may rotate flexible shaft assembly (500), such as to actuate cutter (50) as described above. By way of example only, motor (403) may be associated with vacuum control module (400) and a cart (not shown) in a vacuum control module interface component as taught in U.S. Non-Provisional patent application Ser. No. 12/337,814, entitled "CONTROL MODULE INTERFACE," filed on even date herewith, the disclosure of which is incorporated by reference herein. Of course, the features and functionality of vacuum control module (400) and vacuum canister (401) as described herein are mere examples.

IV. Exemplary Modes of Operation

It will be appreciated in view of the disclosure herein that there are a variety of methods by which biopsy system (2) may be operated. For instance, regardless of the structures or techniques that are used to selectively control communication of fluid (e.g., saline, vacuum, venting, etc.), through conduits (200) or otherwise within biopsy system (2), there are a variety of timing algorithms that may be used. Such timing algorithms may vary based on an operational mode selected by a user. Furthermore, there may be overlap among operational modes (e.g., biopsy system (2) may be in more than one operational mode at a given moment, etc.). In addition to fluid communication timing algorithms being varied based on a selected mode of operation, other operational aspects of biopsy system (2) may vary based on a selected operational mode. Several merely exemplary operational modes exist, while others will be apparent to those of ordinary skill in the art in view of the teachings herein. Any suitable operational mode may be used include for example any suitable mode disclosed in U.S. Pub. No. 2008/0195066, entitled "Revolving Tissue Sample Holder For Biopsy Device," published Aug. 14, 2008, the disclosure of which is incorporated by reference herein.

One exemplary operation of biopsy system (2) will now be explained where needle portion (10) has been inserted into the breast of a patient. With needle portion (10) inserted, lateral and axial vacuum are applied. In particular, a vacuum is communicated through tubes (402, 404). Given the fluid connection of tube (402) with vacuum lumen (40) of outer cannula (12), communication of a vacuum through tube (402) will draw a lateral vacuum relative to cannula lumen (20). Communication of a vacuum through tube (404) will draw an axial vacuum through cutter lumen (52), given the fluid connection of tube (404) to cutter lumen (52) via tissue sample holder (140) in this example.

With the axial and lateral vacuum applied as described above, cutter (50) is retracted axially. The axial retraction of cutter (50) will serve to "open" aperture (16), which results in tissue prolapsing into aperture (16) under the influence of the above-described vacuums. Cutter (50) may dwell in a retracted position for a certain period of time to ensure sufficient prolapse of tissue.

Next, cutter (50) is advanced distally to sever tissue that is prolapsed through aperture (16). As the distal end of cutter (50) passes the distal edge of aperture (16), such that cutter (50) "closes" aperture (16), the prolapsed tissue should be severed and at least initially contained within cutter lumen (52). Transverse openings should be configured such that at least one or more of transverse openings are not covered by cutter (50) when cutter (50) has reached a position to "close" aperture (16). With aperture (16) closed and a vent being provided by transverse openings through tube (402), an axial vacuum being communicated through cutter lumen (52) by tube (404) should create a pressure gradient and draw the severed tissue sample proximally through cutter lumen (52) and into a tissue sample chamber (166) of tissue sample holder (140). Cutter (50) may be reciprocated one or more times through a slight range of motion at a distal position to sever any remaining portions that may have not been completely severed in the first pass of cutter (50).

Before tissue sample is communicated proximally through cutter lumen (52), with aperture (16) being closed by cutter (50), vacuum lumen (40) being vented by tube (402), and an axial vacuum being provided by tube (404) via cutter lumen (52), cutter (50) is retracted slightly to expose a portion of aperture (16) for a short period of time. During this time, saline may be provided at atmospheric pressure to vacuum lumen (40) by tube (402). Further retraction of cutter (50) exposes more transverse openings, thereby increasing fluid communication between vacuum lumen (40) and cannula lumen (20). Retraction of cutter (50) also exposes the pressure of the tissue cavity (from which tissue sample was obtained) to the distal surface of tissue sample. As a result of the slight retraction of cutter (50) in this particular example, the likelihood of atmospheric pressure being applied to the distal face of tissue sample may be increased to help ensure that severed tissue sample does not remain in needle portion (10) (a.k.a. a "dry tap"). Cutter (50) is then fully advanced distally, closing both aperture (16) and all transverse openings of outer cannula (12). Such "closure" of transverse openings may ensure that if medication is applied at this time (between samples) to reduce pain, it will reach the breast cavity through external openings in outer cannula (12) instead of being aspirated through transverse openings and through cutter lumen (52) and tissue sample holder (140).

With the cutter (50) being completely advanced (e.g., such that all transverse openings and aperture (16) are closed), and severed tissue sample being communicated proximally through cutter lumen (52) and into a tissue sample chamber (166) by an axial vacuum drawn by tube (404), biopsy device (100) will be in a ready state. In this ready state, vacuum lumen (40) is vented to atmosphere, and axial vacuum tube (404) is sealed (a.k.a. "dead-headed").

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A biopsy device comprising:
   (a) a body;
   (b) a needle extending distally from the body, wherein the needle is rotatable relative to the body;
   (c) a cutter translatable relative to the needle, wherein the cutter is configured to sever a tissue sample;
   (d) a tissue sample holder, wherein the tissue sample holder is configured to receive the tissue sample severed by the cutter; and
   (e) a manually operated rotation mechanism configured to rotate the tissue sample holder relative to the body such that rotation of the tissue sample holder is independent of the rotation of the needle, wherein the manually operated rotation mechanism includes one or more actuators that are exposed relative to the body distal of the tissue sample holder, wherein the manually operated rotation mechanism is responsive to the one or more actuators to convert lateral movement of the one or more actuators into rotation of the tissue sample holder about a longitudinal axis defined by the tissue sample holder.

2. The biopsy device of claim 1 further comprising a second manually operated rotation mechanism configured to rotate the needle.

3. The biopsy device of claim 2, wherein the second manually operated rotation mechanism comprises a thumbwheel configured to extend through the body such that the thumbwheel is exposed relative to the body.

4. The biopsy device of claim 3, wherein the second manually operated rotation mechanism further comprises a second thumbwheel distal of the body.

5. The biopsy device of claim 1, wherein the needle comprises a lateral tissue receiving opening configured to receive tissue.

6. The biopsy device of claim 5 further comprising a graphical interface configured to display the orientation of the lateral tissue receiving opening of the needle.

7. The biopsy device of claim 1, wherein the tissue sample holder comprises a plurality of discrete tissue sample chambers.

8. The biopsy device of claim 7, wherein the manually operated rotation mechanism is configured to index a chamber of the plurality of discrete tissue sample chambers to align the chamber with the cutter.

9. The biopsy device of claim 8, wherein the manually operated rotation mechanism is configured to advance the tissue sample holder by one chamber.

10. The biopsy device of claim 1, wherein the manually operated rotation mechanism is configured to rotate the tissue sample holder in a first direction and a second direction opposite of the first direction.

11. The biopsy device of claim 1, wherein the manually operated rotation mechanism is configured to rotate the tissue sample holder in a first direction, wherein the manually operated rotation mechanism comprises a rotation restriction assembly, wherein the rotation restriction assembly is configured to prevent the tissue sample holder from rotating in a second direction opposite to the first direction.

12. The biopsy device of claim 11, wherein the rotation restriction assembly comprises a pawl and a resilient member.

13. The biopsy device of claim 1, wherein the one or more actuators of the manually operated rotation mechanism comprises a first actuator positioned on a side of the body and a second actuator positioned on an opposing side of the body.

14. The biopsy device of claim 13, wherein the first actuator is configured to rotate the tissue sample holder in a first direction, wherein the second actuator is configured to rotate the tissue sample holder in a second direction opposite of the first direction.

15. The biopsy device of claim 13, wherein the first and second actuator are both configured to rotate the tissue sample holder in a first direction and a second direction opposite of the first direction.

16. The biopsy device of claim 15, wherein the first and second actuators comprise a first and second thumbwheel.

17. The biopsy device of claim 1, wherein the manually operated rotation mechanism is configured to provide at least one of tactile feedback and audible feedback in response to rotation of the tissue sample holder.

18. The biopsy device of claim 1, wherein the tissue sample holder comprises a plurality of discrete tissue sample chambers, wherein the needle is configured to rotate between a plurality of o'clock positions, wherein the manually operated rotation mechanism is configured to index a tissue sample chamber relative to an o'clock position of the needle.

19. A biopsy device comprising:
   (a) a needle comprising a lateral tissue receiving opening, wherein the needle is rotatable to position the lateral tissue receiving opening at a plurality of o'clock positions;

(b) a cutter translatable relative to the needle, wherein the cutter is configured to sever a tissue sample;

(c) a tissue sample holder, wherein the tissue sample holder is configured to receive the tissue sample severed by the cutter, wherein the tissue sample holder is rotatable about a longitudinal axis defined by the tissue sample holder;

(d) a first actuator configured to manually rotate the tissue sample holder in a first direction;

(e) a second actuator configured to manually rotate the tissue sample holder in a second direction opposite to the first direction; and (f) an actuation assembly comprising a first shaft and a second shaft, wherein the first shaft and the second shaft are together configured to communicate motion of the first actuator and the second actuator to the tissue sample holder.

* * * * *